US005314918A

United States Patent [19]

Frazee et al.

[11] Patent Number: 5,314,918

[45] Date of Patent: May 24, 1994

[54] LEUKOTRIENE ANTAGONISTS

[75] Inventors: James S. Frazee, Sewell, N.J.; John G. Gleason, Downingtown; Ralph F. Hall, Villanova, both of Pa.

[73] Assignee: SmithKline Beecham Corporation, Philadelphia, Pa.

[21] Appl. No.: 864,156

[22] Filed: Apr. 2, 1992

Related U.S. Application Data

[63] Continuation of Ser. No. 366,046, Jun. 14, 1989, abandoned, which is a continuation-in-part of Ser. No. 66,588, Jun. 24, 1987, abandoned.

[51] Int. Cl.[5] .......... A61K 31/19

[52] U.S. Cl. .......... 514/570; 514/438; 514/457; 514/544; 544/335; 546/335; 546/337; 546/342; 548/253; 549/77; 549/79; 549/401; 549/496; 560/9; 560/11; 560/17; 560/18; 562/429; 562/431; 562/432

[58] Field of Search .......... 514/544, 570, 438, 457; 560/9, 11, 17, 18; 562/429, 431, 432; 544/335; 546/335, 337, 342; 548/253; 549/77, 79, 496, 498, 401

[56] References Cited

U.S. PATENT DOCUMENTS

| | | | |
|---|---|---|---|
| 4,609,744 | 9/1986 | Young et al. | 549/402 |
| 4,617,407 | 10/1986 | Young et al. | 549/462 |

FOREIGN PATENT DOCUMENTS

| | | |
|---|---|---|
| 0132367 | 1/1985 | European Pat. Off. . |
| 0202759 | 11/1986 | European Pat. Off. . |
| 59-231065 | 12/1984 | Japan . |
| 1397647 | 6/1975 | United Kingdom . |
| 2092574 | 8/1982 | United Kingdom . |
| 2144422A | 3/1985 | United Kingdom . |

OTHER PUBLICATIONS

*Derwent Patent Abstract* 84–014267/03 of Japanese Patent Appln. 58/206556A, published Dec. 1, 1983.

*Derwent Patent Abstract* 85–026589/05 of European Patent Appln. 132336A, published Jan. 30, 1985.

*Chemical Abstracts* 96(17): 143290n, (1981).

*Chemical Abstracts* 94(9): 64755y, (1981).

*Primary Examiner*—José G. Dees

*Assistant Examiner*—Vera C. Clarke

*Attorney, Agent, or Firm*—James M. Kanagy; Edward T. Lentz; Stuart R. Suter

[57] ABSTRACT

This invention relates to alkanoic acid compounds having phenyl and heteroarylthio substituents which are useful as leukotriene antagonists, processes for the preparation thereof, and pharmaceutical compositions containing such compounds.

This invention also relates to methods of treating diseases in which leukotrienes are a factor by administration of an effective amount of the above compounds or compositions.

15 Claims, No Drawings

LEUKOTRIENE ANTAGONISTS

This is a continuation of U.S. Ser. No. 07/366,046 filed on Jun. 14, 1989 which is a continuation-in-part of U.S. Ser. No. 07/066,588 filed Jun. 24, 1987, both now abandoned.

BACKGROUND OF THE INVENTION

"Slow Reacting Substance of Anaphylaxis" (SRS-A) has been shown to be a highly potent bronchoconstricting substance which is released primarily from mast cells and basophils on antigenic challenge. SRS-A has been proposed as a primary mediator in h=an asthma. SRS-A, in addition to its pronounced effects on lung tissue, also produces permeability changes in skin and may be involved in acute cutaneous allergic reactions. Further, SRS-A has been shown to effect depression of ventricular contraction and potentiation of the cardiovascular effects of histamine.

The discovery of the naturally occurring leukotrienes and their relationship to SRS-A has reinforced interest in SRS-A and other arachidonate metabolites. SRS-A derived from mouse, rat, guinea pig and man have all been characterized as mixtures of leukotriene-$C_4$ ($LTC_4$), leukotriene-$D_4$ ($LTD_4$) and leukotriene-$E_4$ ($LTE_4$), the structural formulae of which are represented below.

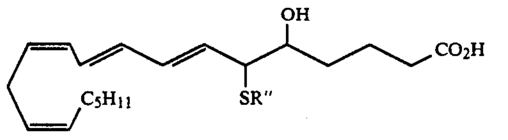

$LTC_4$ R'' = (γ-Glu)Cys—Gly
$LTD_4$ R'' = Cys—Gly
$LTE_4$ R'' = Cys

Leukotrienes are a group of eicosanoids formed from arachidonic acid metabolism via the lipoxygenase pathway. These lipid derivatives originate from $LTA_4$ and are of two types: (1) those containing a sulfido- peptide side chain ($LTC_4$, $LTD_4$, and $LTE_4$), and (2) those that are nonpeptidic ($LTB_4$ ). Leukotrienes comprise a group of naturally occurring substances that have the potential to contribute significantly to the pathogenesis of a variety of inflammatory and ischemic disorders. The pathophysiological role of leukotrienes has been the focus of recent intensive studies.

As summarized by Left, A. M., *Biochemical Pharmacology,* 35, 2, 123-127 (1986) both the peptide and nonpeptide leukotrienes exert microcirculatory actions, promoting leakage of fluid across the capillary endothelial membrane in most types of vascular beds. $LTB_4$ has potent chemotactic actions and contributes to the recruitment and adherence of mobile scavenger cells to the endothelial membrane. $LTC_4$, $LTD_4$ and $LTE_4$ stimulate a variety of types of muscles. $LTC_4$ and $LTD_4$ are potent bronchoconstrictors and effective stimulators of vascular smooth muscle. This vascoconstrictor effect has been shown to occur in pulmonary, coronary, cerebral, renal, and mesenteric vasculatures.

Leukotrienes have been implicated in a number of pulmonary diseases. Leukotrienes are known to be potent bronchoconstrictors in humans. $LTC_4$ and $LTD_4$have been shown to be potent and selective peripheral airway agonists, being more active than histamine. [See Drazen, J. M. et al., *Proc. Nat'l. Acad. Sci. USA,* 77, 7, 4354-4358 (1980).] $LTC_4$ and $LTD_4$ have been shown to increase the release of mucus from human airways in vitro,. [see Marom, Z. et al., *Am. Rev. Respir. Dis.,* 126, 449-451 (1982).] The leukotriene antagonists of the present invention can be useful in the treatment of allergic or non-allergic bronchial asthma or pulmonary anaphylaxis.

The presence of leukotrienes in the sputum of patients having cystic fibrosis, chronic bronchitis, and bronchiectasis at levels likely to have pathophysiological effects has been demonstrated by Zakrzewski et al. [see Zakrzewski, J. T. et al., *Prostaglandins,* 28, 5, 641 (1984).] Treatment of these diseases constitutes additional possible utility for leukotriene antagonists.

Leukotrienes have been identified in the nasal secretions of allergic subjects who underwent in vivo to challenge with specific antigen. The release of the leukotrienes was correlated with typical allergic signs and symptoms. [See Creticos, P. S. et al., *New England J. of Med.,* 310, 25, 1626-1629 (1984).] This suggests that allergic rhinitis is another area of utility for leukotriene antagonists.

The role of leukotrienes and the specificity and selectivity of a particular leukotriene antagonist in an animal model of the adult respiratory distress syndrome was investigated by Snapper et al. [See Snapper, J. R. et al., *Abstracts of Int'l Conf. on Prostaglandins and Related Comp.,* Florence, Italy, p. 495 (June 1986).] Elevated concentrations of LTD4were shown in pulmonary edema fluid of patients with adult respiratory distress syndrome. [See Matthay, M. et al. *J. Clin. Immunol.,* 4, 479-483 (1981).] Markedly elevated leukotriene levels have been shown in the edema fluid of a patient with pulmonary edema after cardiopulmonary bypass. [See Swerdlow, B. N., et al., *Anesth. Analg.,* 65, 306-308, (1986).] LTC and LTD have also been shown to have a direct systemic arterial hypotensive effect and produce vasoconstriction and increased vasopermeability. [See Drazen et al., ibid.] This suggests leukotriene antagonists can also be useful in the areas of adult respiratory distress syndrome, pulmonary edema, and hypertension.

Leukotrienes have also been directly or indirectly implicated in a variety of non-pulmonary diseases in the ocular, dermatologic, cardiovascular, renal, trauma, inflammatory, carcinogenic and other areas.

Further evidence of leukotrienes as mediators of allergic reactions is provided by the identification of leukotrienes in tear fluids from subjects following a conjunctival provocation test and in skin blister fluids after allergen challenge in allergic skin diseases and conjunctival mucosa. [See Bisgaard, H., et al., *Allergy,* 40, 417-423 (1985).] Leukotriene immunoreactivity has also been shown to be present in the aqueous humor of human patients with and without uveitis. The concentrations of leukotrienes were sufficiently high that these mediators were expected to contribute in a meaningful way to tissue responses. [See Parker, J. A. et al., Arch Ophthalmol, 104, 722-724 (1986).] It has also been demonstrated that psoriatic skin has elevated levels of leukotrienes. [See Ford-Hutchinson, *J. Allergy Clin. Immunol.,* 74, 437-440 (1984).] Local effects of intracutaneous injections of synthetic leukotrienes in human skin were demonstrated by Soter et al. [see Soter et al. *J. Clin Invest Dermatol,* 80, 115-119 (1983).] Cutaneous vasodilation with edema formation and a neutrophil infiltrate were induced. Leukotriene synthesis inhibitors or leukotriene antagonists can also be useful in the treatment of ocular or dermatological diseases such as allergic conjunctivitis, uveitis, allergic dermatitis or psoriasis.

Another area of utility for leukotriene antagonists is in the treatment of cardiovascular diseases. Since peptide leukotrienes are potent coronary vasoconstrictors, they are implicated in a variety of cardiac disorders including arrhythmias, conduction blocks and cardiac depression. Synthetic leukotrienes have been shown to be powerful myocardial depressants, their effects consisting of a decrease in contractile force and coronary flow. The cardiac effects of $LTC_4$ and $LTD_4$ have been shown to be antagonized by a specific leukotriene antagonist, thus suggesting usefulness of leukotriene antagonists in the areas of myocardial depression and cardiac anaphylaxis. [See Burke, J. A., et al., *J. Pharmacology and Experimental Therapeutics,* 221, 1, 235–241 (1982).]

$LTC_4$ and $LTD_4$ have been measured in the body fluids of rats in endotoxic shock, but are rapidly cleared from the blood into the bile. Thus leukotrienes are formed in ischemia and shock. Specific inhibitors of leukotriene biosynthesis reduce the level of leukotrienes and therefore reduce manifestations of traumatic shock, endotoxic shock, and acute myocardial ischemia. Leukotriene receptor antagonists have also been shown to reduce manifestations of endotoxic shock and to reduce extension of infarct size. Administration of peptide leukotrienes has been shown to produce significant ischemia or shock. (See Lefer, A. M., *Biochemical Pharmacology,* 35, 2, 123–127 (1986).] Thus further areas of utility for leukotriene antagonists can be the treatment of myocardial ischemia, acute myocardial infarction, salvage of ischemic myocardium, angina, cardiac arrhythmias, shock and atherosclerosis.

Leukotriene antagonists can also be useful in the area of renal ischemia or renal failure. Badr et al. have shown that $LTC_4$ produces significant elevation of mean arterial pressure and reductions in cardiac output and renal blood flow, and that such effects can be abolished by a specific leukotriene antagonist. (See Badr, K. R. et al., *Circulation Research,* 54, 5, 492–499 (1984).] Leukotrienes have also been shown to have a role in endotoxin-induced renal failure and the effects of the leukotrienes selectively antagonized in this model of renal injury. [See Badr, K. F., et al., *Kidney International,* 30, 474–480 (1986).] LTD4 has been shown to produce local glomerular constrictor actions which are prevented by treatment with a leukotriene antagonist. [See Badr, K. F. et al., *Kidney International,* 29, 1, 328 (1986).] LTC has been demonstrated to contract rat glomerular mesangial cells in culture and thereby effect intraglomerular actions to reduce filtration surface area. [See Dunn, M. J. et al., *Kidney International,* 27, 1, 256 (1985).] Thus another area of utility for leukotriene antagonists can be in the treatment of glomerulonephritis.

Leukotrienes have also been indicated in the area of transplant rejection. An increase in cardiac and renal allograft survival in the presence of a leukotriene receptor antagonist was documented by Foegh et al. [See Foegh, M. L. et al. *Advances in Prostaglandin, Thromboxane, and Leukotriene Research,* 13, 209≅217 (1985).] Rejection of rat renal allografts was shown to produce increased amounts of $LTC_4$. [See Coffman, T. M. et al., *Kidney International,* 29, 1, 332 (1986).]

A further area of utility for leukotriene antagonists can be in treatment of tissue trauma, burns, or fractures. A significant increase in the production of cysteinyl leukotrienes was shown after mechanical or thermal trauma sufficient to induce tissue edema and circulatory and respiratory dysfunction. (See Denzlinger, C. et al., *Science,* 230, 330–332 (1985).]

Leukotrienes have also been shown to have a role in acute inflammatory actions. $LTC_4$ and $LTD_4$ have potent effects on vascular caliber and permeability and $LTB_4$ increases leukocyte adhesion to the endothelium. The arteriolar constriction, plasma leakage, and leakocyte adhesion bear close resemblance to the early events in acute inflammatory reactions. [See Dahlen, S. E. et al., *Proc. Natl. Acad. Sci. USA,* 78, 6, 3887–3891 (1981).] Mediation of local homeostasis and inflammation by leukotrienes and other mast cell-dependent compounds was also investigated by Lewis et al. [See Lewis, R. A. et al., *Nature,* 293, 103–108 (1981).] Leukotriene antagonists can therefore be useful in the treatment of inflammatory diseases including rheumatoid arthritis and gout.

Cysteinyl leukotrienes have also been shown to undergo enterohepatic circulation, and thus are indicated in the area of inflammatory liver disease. [See Denzlinger, C. et al., *Prostaglandins Leukotrienes and Medicine,* 21, 321–322 (1986).] Leukotrienes can also be important mediators of inflammation in inflammatory bowel disease. [See Peskar, B. M. et al., *Agents and Actions,* 18, 381–383 (1986).] Leukotriene antagonists thus can be useful in the treatment of inflammatory liver and bowel disease.

Leukotrienes have been shown to modulate IL-1 production by human monocutes. [See Rola-Pleszczynski, M. et al., *J. of Immun.,* 135, 6, 3958–3961 (1985).] This suggests that leukotriene antagonists may play a role in IL-1 mediated functions of monocytes in inflammation and immune reactions.

$LTA_4$ has been shown to be a factor in inducing carcinogenic tumors and is considered a link between acute immunologic defense reactions and carcinogenesis. Leukotriene antagonists can therefore possibly have utility in treatment of some types of carcinogenic tumors. [See Wischnewsky, G. G. et al. *Anticancer Res.* 5, 6, 639 (1985).]

Leukotrienes have been implicated in gastric cytodestruction and gastric ulcers. Damage of gastrointestinal mucosa because of potent vasoconstriction and stasis of blood flow is correlated with increased levels of $LTC_4$. Functional antagonism of leukotriene effects may represent an alternative in treatment of mucosal injury. (See Dreyling, K. W. et al., *British J. Pharmacology,* 88, 236P (1986), and Peskar, B. M. et al. *Prostaglandins,* 31, 2, 283–293 (1986).] A leukotriene antagonist has been shown to protect against stress-induced gastric ulcer in rats. [See Ogle, C. W. et al., *IRCS Med. Sci.,* 14, 114–115 (1986).]

Other areas in which leukotriene antagonists can have utility because leukotrienes are indicated as mediators include prevention of premature labor [See Clayton, J. K. et al., Proceedings of the BPS, 573P. 17–19 December 1984]; treatment of migraine headaches [See Gazzaniga, P. P. et al., *Abstracts Int'l Conf. on Prostaglandins and Related Comp.,* 121, Florence, Italy (June 1986)]; and treatment of gallstones (See Doty, J. E. et al., *Amer. J. of Surgery*, 145, 54–61 (1983) and Marom, Z. et al., *Amer. Rev. Respir. Dis.*, 126, 449–451 (1982).

By antagonizing the effects of $LTC_4$, $LTD_4$ and $LTE_4$ or other pharmacologically active mediators at the end organ, for example, airway smooth muscle, the compounds and pharmaceutical compositions of the instant invention are valuable in the treatment of diseases in subjects, including human or animals, in which leukotrienes are a key factor.

SUMMARY OF THE INVENTION

This invention relates to compounds represented by structural formula (I)

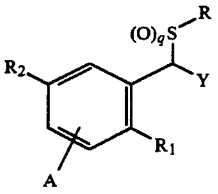

(I)

wherein
q is 0, 1, or 2;
$R_1$ is $(L)_a$—$(CH_2)_b$—$(T)_c$—M
a is 0 or 1;
b is 3 to 14;
c is 0 or 1;
L and T are independently sulfur, oxygen, or $CH_2$ with the proviso that L and T are not sulfur when q is 1 or 2; and
M is c alkyl, ethynyl, trifluoromethyl, isopropenyl, furanyl, thienyl, cyclohexyl or phenyl optionally monosubstituted with Br, Cl, $CF_3$, $C_{1-4}$ alkoxy, $C_{1-4}$ alkyl, methylthio, or trifluoromethylthio;
$R_2$ and A are independently selected from H, $CF_3$, $C_{1-4}$alkyl, $C_{1-4}$alkoxy, F, Cl, Br, I, OH, $NO_2$ or $NH_2$; or, when $R_1$ and A are H, then $R_2$ may also be $(L)_a$—$(CH_2)_b$—$(T)_c$—M wherein a, b, c, L, T, and M are as defined above;
Y is $COR_3$ or

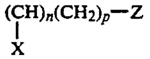

wherein
$R_3$ is OH, NH aryloxy, or $C_{1-6}$ alkoxy;
n is 0 or 1;
p is 0, 1 or 2;
X is H, OH, $C_{1-4}$alkyl, $C_{1-4}$alkoxy, or F; and
Z is $COR_3$, or tetrazolyl;
R is

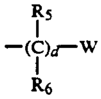

$R_5$ and $R_6$ are each independently hydrogen or $C_{1-4}$alkyl at any point when d is not 0;
d is 0 to 6
W is a six membered aryl or heteroaryl ring selected from phenyl, pyridyl, or pyrimidyl, unsubstituted or substituted with B, C, or D, or W is one of

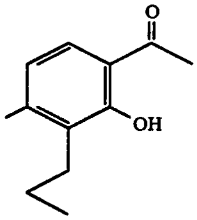

or

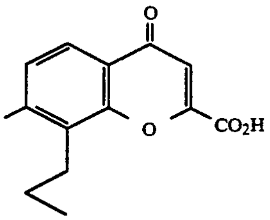

B is

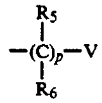

wherein $R_5$ and $R_6$ are each independently hydrogen or $C_{1-4}$ alkyl; p is 0 to 6; V is H, $C_{1-4}$ alkyl, $COR_3$, $SO_3H$, $SO_2H$, $SO_2NH_2$, $COCH_2OH$, $CHOHCH_2OH$, or tetrazolyl, with $R_3$ as defined above;
C and D are independently selected from H, OH, F, Cl, Br, $CF_3$, $C_{1-4}$ alkyl, $C_{1-4}$ alkoxy, methylthio, trifluoromethylthio, $NO_2$, $NH_2$, $NHC_{1-4}$ alkyl, or $C_{1-4}$ alkylCO-; or a pharmaceutically acceptable salt thereof.

This invention further relates to pharmaceutical compositions comprising a nontoxic effective amount of a compound of formula (I), or a pharmaceutically acceptable salt thereof, and a pharmaceutically acceptable carrier or diluent.

This invention also relates to pharmaceutical compositions for inhibiting antigen-induced respiratory anaphylaxis comprising a nontoxic effective amount of a compound of formula (1), or a pharmaceutically acceptable salt thereof, an histamine $H_1$ -receptor antagonist, and a pharmaceutically acceptable carrier or diluent.

This invention also relates to a method of treating diseases in which leukotrienes are a factor in a subject in need thereof comprising administering to such subject a nontoxic effective amount of one of the above described pharmaceutical compositions.

This invention also relates to a process for preparation of the compounds of Formula (1) of known chirality comprising a) reacting an appropriate diester with a strong base to generate an intermediate thiol, and b) reacting the thiol with an alkylating agent or Michael acceptor, i.e., $\alpha$, $\beta$ unsaturated carbonyl compound to yield a compound of Formula (I).

DETAILED DESCRIPTION OF THE INVENTION

This invention relates to compounds represented by structural formula (I)

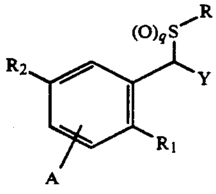

(I)

wherein
q is 0, 1, or 2;
$R_1$ is $(L)_a$—$(CH_2)_b$—$(T)_c$—M a is 0 or 1;
b is 3 to 14;
c is 0 or 1;
L and T are independently sulfur, oxygen, or $CH_2$ with the proviso that L and T are not sulfur when q is 1 or 2; and
M is $C_{1-4}$ alkyl, ethynyl, trifluoromethyl, isopropenyl, furanyl, thienyl, cyclohexyl or phenyl optionally monosubstituted with Br, Cl, $CF_3$, $C_{1-4}$ alkoxy, $C_{1-4}$ alkyl, methylthio, or trifluoromethylthio;
$R_2$ and A are independently selected from H, $CF_3$, $C_{1-4}$alkyl, $C_{1-4}$alkoxy, F, Cl, Br, I, OH, $NO_2$ or $NH_2$; or, when $R_1$ and A are H, then $R_2$ may also be $(L)_a$—$(CH_2)_b$—$(T)_c$—M wherein a, b, c, L, T, and M are as defined above;
Y is $COR_3$ or

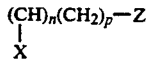

wherein
$R_3$ is OH, NH aryloxy, or $C_{1-6}$ alkoxy;
n is 0 or 1;
p is 0, 1 or 2;
X is H, OH, $C_{1-4}$ alkyl, $C_{1-4}$ alkoxy, or F; and
Z is $COR_3$ or tetrazolyl;
R is

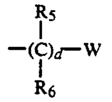

$R_5$ and $R_6$ are each hydrogen or $C_{1-4}$ alkyl at any point when d is not 0;
d is 0 to 6;
W is a six-membered aryl or heteroaryl ring selected from phenyl, pyridyl, or pyrimidyl, unsubstituted or substituted by one or more of B, C, or D, or W is one of

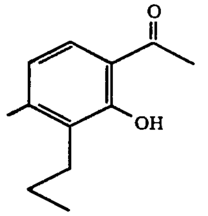
or
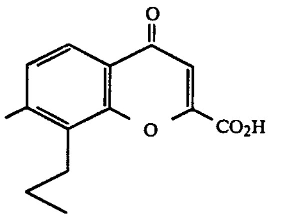

B is

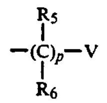

wherein
$R_5$ and $R_6$ are each hydrogen or $C_{1-4}$ alkyl;
p is 0 to 6;
V is H, $C_{1-4}$alkyl, $COR_3$, $SO_3H$, $SO_2H$, $SO_2NH_2$, $COCH_2OH$, $CHOHCH_2OH$, or tetrazolyl, with $R_3$ as defined above;
C and D are independently selected from H, OH, F, Cl, Br, $C_{1-4}$alkyl, $C_{1-4}$alkoxy, methylthio, trifluoromethylthio, $NO_2$, $NH_2$ $NHC_{1-4}$alkyl, or $C_{1-4}$alkylCO-;
or a pharmaceutically acceptable salt thereof.

A particular class of compounds of this invention are those represented by structural formula (II)

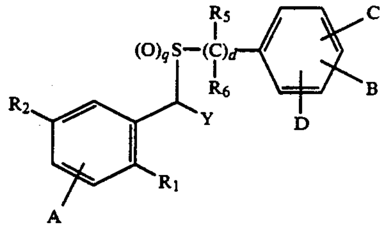
(II)

wherein $R_1$, $R_2$, A, B, C, D, $R_5$, $R_6$, q, d and Y are as defined above.

A subgeneric class of these compounds are those represented by structural formula (III)

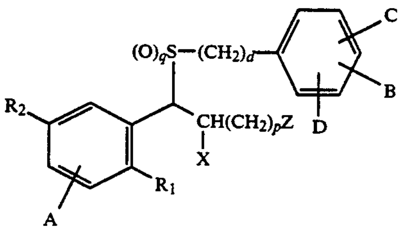
(III)

wherein X, Z, $R_1$, $R_2$, A, B, C, D, q, p, and d are as defined above.

A particular group of the subgeneric class represented by formula (III) are the compounds represented by structural formula (IIIA)

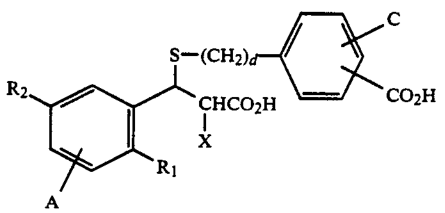
(IIIA)

wherein
X is OH, H, or $OCH_3$;
d is 0 or 1; and
$R_1$, $R_2$, A, and C are as defined above.

The compounds of formulae (III) and (IIIA) are exemplified by the following compounds:

(1) 2-Hydroxy-3-(2-carboxyphenylthio)-3-[2-(8-phenyloctyl)phenyl]propionic acid;
(2) 2(S)-Hydroxy-3(R)-(2-carboxyphenylmethylthio)-3-12-(8-phenyloctyl)phenyl]propionic acid;
(3) 2(S)-Hydroxy-3(R)-(3-carboxyphenylmethylthio)-3-[2-(8-phenyloctyl)phenyl]propionic acid;
(4) 2-Hydroxy-3-(3-carboxyphenylthio)-3-[2-(8-phenyloctyl)phenyl]propionic acid;
(5) 2-Hydroxy-3-(4-carboxyphenylthio)-3-[2-(8-phenyloctyl)phenyl]propionic acid;
(6) 2-Hydroxy-3-(4-carboxy-2-methoxyphenylmethylthio)-3-[2-(8-phenyloctyl)phenyl]propionic acid; and
(7) 2-Hydroxy-3-(4-carboxyphenylmethylthio)-3-(2-(8-phenyloctyl)phenyl]propionic acid;

(8) 2-Hydroxy-3-(2-fluoro-4-carboxyphenylmethylthio)-3-(2-(8-phenyloctyl)phenyl]propionic acid;

(9) 2-Methoxy-3-(4-carboxyphenylthio)-3-[2-(8-phenyloctyl)phenyl]propionic acid;

(10) 2-Hydroxy-3-(4-hydroxyphenylthio)-3-[2-(8-phenyloctyl)phenyl]propionic acid; and

(11) 2-Methoxy-3-14-carboxy-2-methoxyphenylmethylthio)-3-(2-(8-phenyloctyl)phenyl]propionic acid.

A second subgeneric class of the compounds of formula (II) are those represented by structural formula (IV)

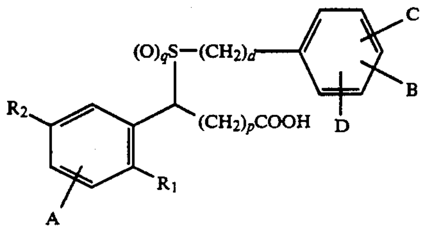

(IV)

wherein $R_1$, $R_2$, A, B, C, D, q, and d are as defined above and p is 1 or 2.

The compounds of formula (IV) are exemplified by the following compounds:

(1) 3-(2-carboxyphenylthio)-3-12-(8-phenyloctyl) phenyl]propionic acid;

(2) 3-(2-carboxyphenylmethylthio)-3-12-(8-phenyloctyl)phenyl]propionic acid; and (3) 3-(4-carboxy-2-methoxyphenylmethylthio)-3-[2-(8-phenyloctyl)phenyl]propionic acid.

A third subgeneric class of the compounds of formula (II) are those represented by structural formula (V)

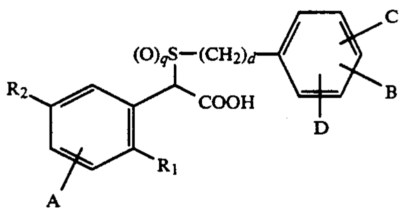

(V)

wherein $R_1$, $R_2$, A, B, C, D, q, and d are as defined above.

The compounds of formula (V) are exemplified by the following compounds.

(1) 2-(2-carboxyphenylthio)-2-[2-(8-phenyloctyl) phenyl]acetic acid;

(2) 2-(2-carboxyphenylmethylthio)-2-[2-(8-phenyloctyl)phenyl]acetic acid;

(3) 2-(3-carboxyphenylmethylthio)-2-[2-(8-phenyloctyl)phenyl]acetic acid;

A further particular class of compounds of this invention are those represented by structural formula (VI)

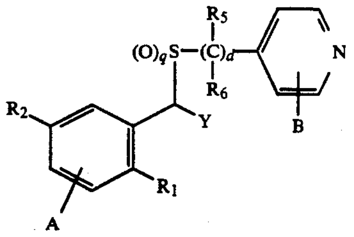

(VI)

wherein $R_1$, $R_2$, A, B, Y, $R_5$, $R_6$, q, and d are as defined above for formula (I).

The compounds of formula (VI) are exemplified by the following compounds.

(1) 2-Hydroxy-3-(2-carboxy-4-pyridylthio)-3-[2-(8-phenyloctyl)phenyl]propionic acid;

(2) 3-(2-carboxy-4-pyridylthio)-3-[2-(8-phenyloctyl)-phenyl]propionic acid; and (3) 2-(3-carboxy-4-pyridylmethylthio)-2-(8-phenyloctyl)phenyl]acetic acid;

A further particular class of compounds of this invention are those represented by structural formula (VII)

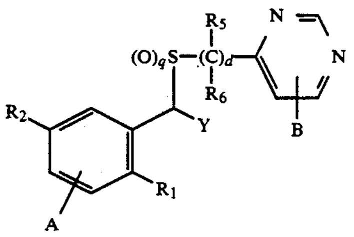

(VII)

wherein $R_1$, $R_2$, A, B, $R_5$, $R_6$, Y, and d are as defined above.

The compounds of formula (VII) are exemplified by the following compounds.

(1) 2-Hydro-3-(2-carboxy-4-pyrimidylthio)-3-[2-(8-phenyloctyl)phenyl]propionic acid;

(2) 3-(2-carboxy-4-pyrimidylthio)-3-[2-(8-phenyloctyl)-phenyl]propionic acid; and (3) 2-(2-carboxy-4-pyrimidylmethylthio)-2-[2-(8-phenyloctyl)phenyl]acetic acid;

The compounds of the present invention, which contain one or two carboxylic acid groups, are capable of forming salts with pharmaceutically acceptable bases, according to procedures well known in the art. Such acceptable bases include organic and inorganic bases, such as ammonia, arginine, organic amines, alkaline earth and alkali metal bases. Of particular utility are the potassium, sodium, ammonium, magnesium and calcium salts.

Some of the compounds of formula (1) contain one or two asymmetric centers. This leads to the possibility of two or four stereoisomers for each such compound. The present invention includes all such stereoisomers, racemates, or mixtures thereof.

The compounds of the formula (I) wherein Y is $CO_2H$ are conveniently prepared from an aldehyde precursor of the following structural formula (VIII)

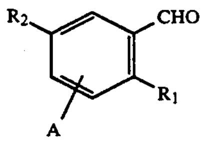

(VIII)

wherein $R_1$ and $R_2$are described above. A compound of formula (VIII) is treated with trimethylsilyl cyanide in the presence of zinc iodide at low temperatures in an inert solvent to form the trimethylsilyl-protected cyanohydrin. Treatment of this with gaseous hydrogen chloride in methanol provides the methyl 2-hydroxyacetate derivative which is converted to the 2-chloroacetate with thionyl chloride. This valuable intermediate is then reacted with a substituted thiol selected to give, after removal of ester protective groups, a product of formula (I).

The compounds of the formula (I) wherein Y is $CH_2CO_2H$ or $CH(X)CO_2H$ wherein X is H, $C_{1-4}$alkyl, or $C_{1-4}$alkoxy are prepared by reacting the appropriate aldehyde of the formula (VIII) and an esterified bromoacetate, conveniently t-butyl bromoacetate, with a mixture of diethyl aluminum chloride, zinc dust and a catalytic amount of cuprous bromide at low temperatures in an inert solvent to give the esterified 3-hydroxypropionate derivative which is reacted directly with a substituted thiol in trifluoroacetic acid. Alternatively, a mixture of trimethyl borate and zinc in tetrahydrofuran may be used to prepare the 3-hydroxypropionate derivative. Alternatively an aldehyde of formula (VIII) may be reacted at low temperature with the lithium salt of an esterified acetic acid, conveniently t-butylacetate, in an inert solvent to give the esterified 3-hydroxyprouionate derivative. By employing an esterified 2-bromopropionate in the above reaction with an aldehyde (VIII), the compounds of the formula (I) wherein Y is $CH(CH_3)CO_2H$ are obtained.

To prepare the compounds of formula (I) wherein q is 1 or 2, the appropriate thio product is conveniently oxidized with sodium periodate or meta-chloroperbenzoic acid to obtain the sulfoxide or sulfone product.

Alternatively, the compounds of the formula (I) wherein Y is $CH(X)CO_2H$ wherein X is H, $C_{1-4}$alkyl, $C_{1-4}$alkoxy, or fluoro are prepared from a propenoate precursor of the following structural formula (IX)

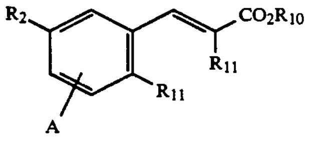

(IX)

wherein $R_1$ and $R_2$ are described above, Rio is a standard ester protective group, such as t-butyl, and $R_{11}$ is H, $C_{1-4}$alkyl, $C_{1-4}$alkoxy, or fluoro. A compound of formula (IX) is reacted with a mixture of alkali metal alkoxide, such as sodium methoxide, and substituted thiol to give, after removal of the ester protective group, products of formula (I).

The propenoate precursors of formula (IX) are prepared from the corresponding aldehydes of formula (VIII) by general procedures such as reaction with an alkyl (triphenylphosphoranylidene)acetate or by conversion of the aldehyde to a 3-hydroxypropionate derivative, as described above, followed by an elimination reaction to form the double bond. Additionally, the propenoate precursor is obtained from a 3-methanesulfonyloxypropionate derivative by treatment with triethylamine.

The compounds of the formula (I) wherein Y is $CH(OH)(CH_2)_pCO_2H$ are prepared from an epoxide precursor of the following structural formula (X)

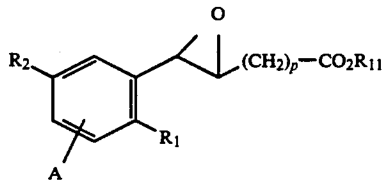

(X)

wherein $R_1$, $R_2$, A and p are described above, and $R_{11}$ is lower alkyl, such as methyl or ethyl. A compound of formula (X) is reacted in an aprotic solvent with triethylamine and a substituted thiol selected to give, after removal of ester protective groups, a product of formula (I).

The epoxide precursors of formula (X) where p is 2 are prepared by reaction of the Grignard derivative of a bromobenzene compound of the formula (XI)

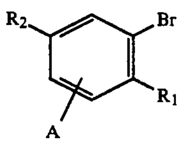

(XI)

with acrolein to give the corresponding enol derivative which is treated with a trialkylorthoacetate, followed by epoxidation using m-chloroperbenzoic acid.

The epoxide precursors of formula (X) where p is 0 are prepared by reaction of an aldehyde of the formula (VIII) with a lower alkyl chloroacetate and an alkali metal alkoxide, such as sodium methoxide.

The compounds for formula (I) wherein Y is $$\underset{\displaystyle |\atop OH}{CH}(CH_2)_pCOOH$$

can also be prepared from an ester of the following structural formula (XII)

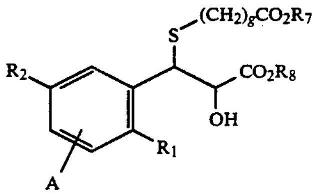

(XII)

wherein $R_7$ and $R_8$ are the same or different and are $C_{1-6}$ alkyl, and g is 2. A compound of formula (XII) is reacted with sodium hydride in an inert solvent followed by reaction with a substituted benzyl bromide to yield a product of formula (I).

The compounds of the formula (1) wherein Y is $(CH_2)_3CO_2$ are prepared from a tetrahydro-4H-pyran-2-one precursor of the following structural formula (XIII)

(XIII)

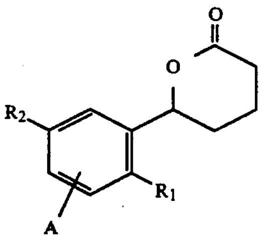

wherein $R_1$ and $R_2$ are described above. A compound of formula (XIII) is reacted with a mixture of zinc-iodide and a substituted thiol in an inert solvent or with a substituted thiol in trifluoroacetic acid to give, after removal of any ester protective group, a product of formula (I).

The tetrahydro-4H-pyran-2-one precursors of formula (XIII) are prepared by reaction of the Grignard derivative of the bromobenzene compound of formula (XI) with chloro titanium tri-isopropoxide followed by reaction with 5-oxovalerate alkyl ester.

The aldehydes of the formula (VIII) are known or readily prepared utilizing the general procedures described as follows.

The aldehyde precursors to the compounds of the formula (I) wherein $R_1$ is, for example, an alkyl radical containing 8 to 13 carbon atoms are prepared from the appropriate 2-alkoxyphenyl-4,4-dimethyloxazoline [see Meyers et al. *J Org. Chem.*, 43 1372 (1978)].

The aldehyde precursors of the compounds of the formula (1) wherein $R_1$ is, for example, an alkoxy radical containing 7 to 12 carbon atoms are prepared by the O-alkylation of the appropriate 2-hydroxybenzaldehyde with the corresponding alkylating agent.

The aldehyde precursors to the compounds of the formula (I) wherein $R_1$ is a 1-alkynyl radical containing 10 to 12 carbon atoms are prepared by coupling a 2-halobenzaldehyde with the appropriate 1-alkyne in the presence of cuprous iodide and $(Ph_3)_2\ PdCl_2$. [See Hagihara, et al. *Synthesis*, 627, (1980)]. The catalytic hydrogenation of these alkynyl containing precursors under standard conditions affords the aldehyde precursors of the compounds of the formula (I) wherein $R_1$ is an alkyl or phenylalkyl radical.

The alkylthio containing aldehyde precursors of the compounds of the formula (I) are prepared by the reaction of the appropriately substituted o-haloalkylthiobenzene with magnesium and dimethylformamide.

The phenylthioalkyl containing aldehyde precursors of the compounds of the formula (I) are prepared by the reaction of the appropriately substituted haloalkyl benzaldehyde with a thiophenol and triethylamine.

The heteroaryl mercaptan precursors necessary to prepare the compounds of formula (I) are known compounds and are conveniently prepared employing standard chemical reactions. The mercapto derivatives of these precursors are prepared according to known methods. These mercaptans are reacted as described above to yield compounds of formula (I).

Appropriate modifications of the general processes disclosed, and as further described in the Examples provided hereinbelow, furnish the various compounds defined by formula (I).

This invention further relates to a process for the preparation of the compounds of Formula (I) of known chirality comprising reacting a diester with a strong base to generate a thiol which is then reacted with an alkylating agent or Michael acceptor to yield the desired compound.

An appropriate diester is represented by Formula (XIV)

(XIV)

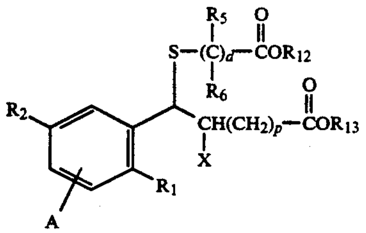

wherein
d is 2;
X is OH;
one of $R_5$ or $R_6$ adjacent to the ester group is H and the other is H or $C_{1-4}$alkyl; and $R_1$, $R_2$, A, and p are as defined in Formula (I) and $R_{12}$ and $R_{13}$ are independently selected from $C_{1-6}$ alkyl. Suitable strong bases include those such as sodium methoxide, sodium hydride, sodium amide, lithium diisopropyl amide or others. The reaction is conducted in an aprotic solvent such as tetrahydrofuran, dimethylsulfoxide, or N,N-dimethylformamide at ambient temperature and pressure. The resulting intermediate thiol of known chirality is represented by Formula (XV)

(XV)

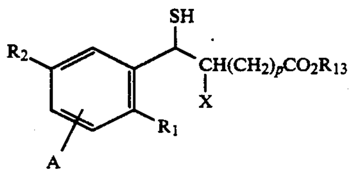

wherein $R_1$, $R_2$, $R_{13}$, A, X, and p are as defined in Formula (XIV).

The thiol of Formula (XV) is reacted with an alkylating agent or Michael acceptor to yield a compound of Formula (1). Suitable alkylating agents include alkyl halides such as alkyl bromide or alkyl iodide. Benzyl halides are especially suitable to prepare compounds of Formula (I). The reaction is conducted in an aprotic solvent at ambient temperature and pressure. Suitable Michael acceptors include compounds which undergo nucleophilic addition. Examples include compounds containing carbonyl, carboalkoxy, or cyano groups conjugated with a double or triple bond. Carbonyl compounds or alkynes represented by the following structural formulae are especially suitable

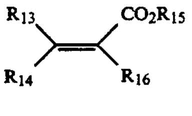

or $HC{\equiv}C.CO_2R_{17}$ wherein $R_{13}$, $R_{14}$, and $R_{16}$ are independently selected from hydrogen or $C_{1-6}$ alkyl, $R_{15}$ and $R_{17}$ are independently selected from H, aryl, or $C_{1-4}$alkyl. The reaction is conducted in an aprotic solvent at ambient temperature and pressure.

The leukotriene antagonist activity of the compounds of this invention is measured by the ability of the compounds to inhibit the leukotriene induced contraction Of guinea pig tracheal tissues in vitro. The following methodology was employed:

In vitro: Guinea pig (adult male albino Hartley strain) tracheal spiral strips of approximate dimensions 2 to 3 mm, cross-sectional width and 3.5 cm length were bathed in modified Krebs buffer in jacketed 10 ml tissue bath and continuously aerated with 95% $O_2$/5% $CO_2$. The tissues were connected via silk suture to force displacement transducers for recording isometric tension. The tissues were equilibrated for 1 hr., pretreated for 15 minutes with meclofenamic acid (1 uM) to remove intrinsic prostaglandin responses, and then pretreated for an additional 30 minutes with either the test compound or vehicle control. A cumulative concentration-response curve for $LTD_4$ on triplicate tissues was generated by successive increases in the bath concentration of the $LTD_4$. In order to minimize intertissue variability, the contractions elicited by $LTD_4$were standardized as a percentage of the maximum response obtained to a reference agonist, carbachol (10 uM).

Calculations: The averages of the triplicate $LTD_4$ concentration-response curves both in the presence and absence of the test compound were plotted on log graph paper. The concentration of $LTD_4$ needed to elicit 30% of the contraction elicited by carbachol was measured and defined as the $EC_{30}$. The $-\log K_B$ value for the test compound was determined by the following equations:

1. $$\frac{EC_{30}\text{ (presence of test compound)}}{EC_{30}\text{ (presence of vehicle control)}} = \text{dose ratio} = X$$

2. $K_B$ = concentration of test compound/$(X-1)$

The compounds of this invention possess biosignificant antagonist activity against leukotrienes, primarily leukotriene $D_4$. The antagonist activity of representative compounds of this invention is listed in Table I. The $-\log K_B$ values were calculated from the above protocol. Where compounds were tested more than once, the $-\log K_B$ values given here represent the current average data.

TABLE I

Leukotriene Antagonist Activity
Compounds of Formula (III) wherein $R_2$, A, C, and D are hydrogen, q is O, p is O, Z is $CO_2H$, and $R_1$ is 8-phenyloctyl

| | d | B | X | In Vitro $-\text{Log } K_B$ |
|---|---|---|---|---|
| 1) | 0 | 2-$CO_2H$ | OH | 5.5 |
| 2) | 1 | 2-$CO_2H$ | OH | 6.2 |
| 3) | 1 | 3-$CO_2H$ | OH | 6.6 |
| 4) | 0 | 3-$CO_2H$ | OH | 7.0 |
| 5) | 0 | 4-$CO_2H$ | OH | 7.6 |
| 6) | 1 | 2-$OCH_3$, 4-$CO_2H$ | OH | 7.9 |
| 7) | 1 | 4-$CO_2H$ | OH | 7.1 |
| 8) | 1 | 2-F, 4-$CO_2H$ | OH | 7.8 |
| 9) | 0 | 4-$CO_2H$ | $OCH_3$ | 7.6 |
| 10) | 0 | 4-OH | OH | 5.9 |
| 11) | 1 | 4-$CO_2H$ 2-$OCH_3$ | $OCH_3$ | 7.4 |
| 12) | 1 | 4-$CO_2H$ 2-$OCH_3$ | H | 7.5 |
| 13) | 1 | 2-$OCH_3$ 5-$CO_2H$ | OH | 6.5 |

Pharmaceutical compositions of the present invention comprise a pharmaceutical carrier or diluent and an amount of a compound of the formula (I) or a pharmaceutically acceptable salt, such as an alkali metal salt thereof, sufficient to produce the inhibition of the effects of leukotrienes, such as symptoms of asthma and other hypersensitivity diseases.

When the pharmaceutical composition is employed in the form of a solution or suspension, examples of appropriate pharmaceutical carriers or diluents include: for aqueous systems, water; for non-aqueous systems, ethanol, glycerin, propylene glycol, corn oil, cottonseed oil, peanut oil, sesame oil, liquid paraffins and mixtures thereof with water; for solid systems, lactose, kaolin and mannitol; and for aerosol systems, dichlorodifluoromethane, chlorotrifluoroethane and compressed carbon dioxide. Also, in addition to the pharmaceutical carrier or diluent, the instant compositions may include other ingredients such as stabilizers, antioxidants, preservatives, lubricants, suspending agents, viscosity modifiers and the like, provided that the additional ingredients do not have a detrimental effect on the therapeutic action of the instant compositions.

The nature of the composition and the pharmaceutical carrier or diluent will, of course, depend upon the intended route of administration, i.e. parenterally, topically or by inhalation.

In general, particularly for the prophylactic treatment of asthma, the compositions will be in a form suitable for administration by inhalation. Thus the compositions will comprise a suspension or solution of the active ingredient in water for administration by means of a conventional nebulizer. Alternatively the compositions will comprise a suspension or solution of the active ingredient in a conventional liquified propellant or compressed gas to be administered from a pressurized aerosol container. The compositions may also comprise the solid active ingredient diluted with a solid diluent for administration from a powder inhalation device. In the above compositions, the amount of carrier or diluent will vary but preferably will be the major proportion of a suspension or solution of the active ingredient. When the diluent is a solid it may be present in lesser, equal or greater amounts than the solid active ingredient.

For parenteral administration the pharmaceutical composition will be in the form of a sterile injectable solution or an aqueous or nonaqueous liquid suspension.

For topical administration the pharmaceutical composition will be in the form of a cream or ointment.

Usually a compound of formula I is administered to an animal subject in a composition comprising a nontoxic amount sufficient to produce an inhibition of the symptoms of an allergic response. When employed in this manner, the dosage of the composition is selected from the range of from 350 mg. to 700 mg. of active ingredient for each administration. For convenience, equal doses will be administered 1 to 4 times daily with the daily dosage regimen being selected from about 350 mg. to about 2800 mg.

The pharmaceutical preparations thus described are made following the conventional techniques of the pharmaceutical chemist as appropriate to the desired end product.

Included within the scope of this disclosure is the method of inhibiting the symptoms of an allergic response resulting from a mediator release which comprises administering to an animal subject a therapeutically effective amount for producing said inhibition of a compound of formula 1. preferably in the form of a pharmaceutical composition. The administration may be carried out in dosage units at suitable intervals or in single doses as needed. Usually this method will be practiced when relief of allergic symptoms is specifically required. However, the method is also usefully carried out as continuous or prophylactic treatment. It is within the skill of the art to determine by routine experimentation the effective dosage to be administered from the dose range set forth above, taking into consideration such factors as the degree of severity of the allergic condition being treated, and so forth.

Compounds of this invention, alone and in combination with a histamine $H_1$-receptor antagonist, inhibit antigen-induced contraction of isolated, sensitized guinea pig trachea (a model of respiratory anaphylaxis). Exemplary of histamine $H_1$-receptor antagonists are mepyramine, chlorpheniramine, and 2-[4-(5-bromo-3-methylpyrid-2-yl)butylaminol-5-1(6-methyl-pyrid-3-yl)methyl]-4-pyrimidone, and other known H receptor antagonists.

Pharmaceutical compositions, as described hereinabove, of the present invention also comprise a pharmaceutical carrier or diluent and a combination of a compound of the formula (I) or a pharmaceutically acceptable salt thereof, and an histamine $H_1$-receptor antagonist in amounts sufficient to inhibit antigen-induced respirator anaphylaxis. The above-defined dosage of a compound of formula I is conveniently employed for this purpose and the known effective dosage for the histamine $H_1$- receptor antagonist. The methods of administration described above for the single active ingredient can similarly be employed for the combination with a histamine $H_1$-receptor antagonist.

The following examples illustrate the preparation of the compounds of this invention and their incorporation into pharmaceutical compositions and as such are not to be considered as limiting the invention set forth in the claims appended hereto.

EXAMPLE 1

Preparation of 2-Hydroxy-3-(2-carboxyphenylthio)-3-[2-(8-phenyloctyl)phenyl]propionic acid (a) 2-(8-Phenyloctyl)benzaldehyde A solution of 8-phenyloctanoic acid (19.8 mmol) in sieve dried tetrahydrofuran (5 ml) was reduced with diborane in tetrahydrofuran (30 ml, 29.1 mmol) at 0° C. for 4 hours to give 8-phenyloctanol. To an ice cold solution of the octanol (ca. 19.8 mmol) and carbon tetrabromide (21.98 mmol) in methylene chloride (50 ml) was added triphenylphosphine (22.30 mmol) in methylene chloride (50 ml) and the resulting solution was stirred for 2.5 hours. The volatiles were evaporated and the residue was taken up in ether (100 ml), cooled in ice, and filtered. The filtrate was evaporated and distilled to afford 8-phenyloctyl bromide as an oil.

To 8-phenyloctylmagnesium bromide (from 24.25 mmol of 8-phenyloctyl bromide and 21.27 mmol of magnesium) in distilled tetrahydrofuran (40 ml) was added 2-(2-methoxyphenyl)-4,4-dimethyloxazoline (17.10 mmol) [A. I. Meyers et al., *J. org. Chem.*, 43, 1372 (1978)] in tetrahydrofuran (20 ml). After stirring for 24 hours, the reaction mixture was worked up to yield 2-12-(8-phenyloctyl)phenyl]-4,4-dimethyloxazoline as an oil. A solution of the oxazoline (11.58 mmol) in methyl iodide (20 ml) was refluxed under argon for 18 hours. Removal of the volatiles afforded the corresponding 3,4,4-trimethyloxazolinium iodide as a white solid (mp 76.5°-78° C.).

To an ice cold solution of the iodide (9.46 mmol) in methanol (35 ml) was added in portions sodium borohydride (9.20 mmol). The reaction mixture was allowed to stir for 30 minutes and was then quenched with 5 percent sodium hydroxide (50 ml). The reaction mixture was extracted with diethyl ether (2×50 ml) and the extract was washed with brine (50 ml) and dried over anhydrous magnesium sulfate and filtered. Evaporation of the filtrate afforded an oil which was dissolved in acetone (50 ml) and 3N hydrochloric acid (10 ml) was added. The mixture was flushed with argon and stirred for 16 hours at ambient temperature. The volatiles were removed under vacuum and the residue partitioned between diethyl ether (50 ml) and water (50 ml). The aqueous phase was extracted with more diethyl ether (50 ml). The combined organic phase was washed with brine (50 ml) and dried over anhydrous magnesium sulfate. Evaporation of the organic phase yielded an oil which was purified by flash chromatography over silica gel with 2 percent ethyl acetate in hexane as eluant to afford the desired product as a colorless oil.

Analysis for $C_{21}H_{26}O$: Calculated: C, 85.67; H, 8.90. Found: C, 85.12, 85.22; H, 8.94, 8.96.

(b) Alternative preparation of 2-(8-phenyloctyl)benzaldehyde

A solution of 5-hexynyl alcohol (102 mmol) in pyridine (150 ml), under argon, was cooled to 0° C. and p-toluenesulfonyl chloride (204 mmol) was added. The reaction mixture was kept at about 40C for 18 hours, poured into ice-water and then taken up in ether. The ether extract was washed with cold 10% hydrochloric acid, water and brine. The organic layer was dried and concentrated in vacuo to give 5-hexynyl p-toluenesulfonate. A solution of phenylacetylene (97 mmol) in tetrahydrofuran (200 ml) containing a trace of triphenylmethane was cooled to 0° C. and then n-butyl lithium (37.3 ml of 2.6 mol in hexane) was added dropwise. The resulting solution was stirred at 0° C. for 10 minutes and hexamethylphosphoramide (21 ml) was added dropwise. After stirring for 10 minutes a solution of 5-hexynyl p-toluenesulfonate (97.1 mmol) in tetrahydrofuran (200 ml) was added. The reaction mixture was stirred at room temperature for 18 hours, diluted I with ether and the organic layer was washed with water and brine. The dried organic solution was concentrated and the product was purified by flash chromatography to give 1-phenylocta-1,7-diyne. A mixture of this compound (43 mmol), 2-bromobenzaldehyde (35.8 mmol), cuprous iodide (0.5 mmol) and bis(triphenylphosphine) palladium (II) chloride (0.7 mmol) in triethylamine (100 ml) was heated in an oil bath (95° C.) for one hour. The reaction mixture was cooled to 0° C., filtered and the filtrate was concentrated. The residue was dissolved in ether, washed with 10% hydrochloric acid, water and brine. The organic layer was dried and concentrated to give a product which was purified by flash chromatography to yield 2-(8-phenyl-1,7-octadiynyl)benzaldehyde. A solution of this compound (24.1 mmol) in ethyl acetate (100 ml) and 10% palladium on charcoal (1 g) was hydrogenated (40 psi of hydrogen) at room temperature for 15 minutes. The catalyst was filtered off and the filtrate concentrated to give the 2-(8-phenyloctyl)-benzaldehyde.

(c) Methyl trans-3-12-(8-Phenyloctyl)phenyl]-2,3-epoxypropionate

The compound of Example 1(a) or (b) (2.94 g, 10 mmol) was dissolved in diethyl ether (25 ml) and the solution was stirred under argon at 0° C. Methyl chloroacetate (1.32 ml, 15 mmol) was added, followed by the addition of sodium methoxide (810 mg, 15 mmol). The mixture was stirred for 2.5 hours at ice bath temperature. A small quantity of water was added, the ether phase separated, dried over anhydrous sodium sulfate, filtered and evaporated. The residue was flash chromatographed on 80 grams of silica gel eluted with 5-30% ethyl acetate/hexane to give the product.

(d) Methyl 2-hydroxy-3-(2-carboxyphenylthio)-3-[2-(8-phenyloctyl)phenyl]propionate A solution of the compound of Example 1(c) (0.51 gm, 1.39 mmol), 2-mercaptobenzoic acid (0.24 gm, 1.53 mmole) and triethylamine (0.31 gm, 3.06 mmol) in 10 ml of methanol were stirred overnight at 221 under argon. The mixture was poured into water, acidified with 1N hydrochloric acid, and extracted with diethylether. The extracts were dried and the solvent evaporated. The residue was chromatographed on silica gel to remove starting materials and the product eluted with a mixture of ethyl acetate, hexane and methanol (60:40:2.5). The solvents were evaporated, and the residue recrystallized from methanol, to yield the product, 230 mg (32%).

(e) 2-Hydroxy-3-(2-carboxyphenylthio)-3-12-(8-phenyloctyl)phenyl]propionic acid

A suspension of the compound of Example 1(d) (0.23 gm, 0.44 mmol), 5 ml of methanol, 2 ml of water and 2 ml of 2.5N sodium hydroxide was heated at 951 for 10 minutes, and stirred at 221 for 2 hr. The mixture was diluted with 20 ml of water, and filtered. The filtrate was acidified, and extracted with ethyl acetate. The extracts were washed with water, dried, and the solvent evaporated. The residue was recrystallized from acetonitrile and gave the desired product, 182 mg (82%).

nmr ($CDCl_3$/$Me_2CO$) 9.70 ppm (broad s, 3H), 7.05-8.06 (m, 13H), 5.28 (d, 1H), 4.76 (d, 1H), 2.40-3.05 (m, 4H), 1.13-1.72 (m, 12H).

Similarly, the following compounds are prepared according to the general method of Example 1 from the 2-(2-methoxyphenyl)-4,4-dimethyloxazoline and the appropriate alkyl halide:

2-Hydroxy-3-(2-carboxyphenylthio)-3-[2-(3-phenylpropyl)phenyl]propionic acid;

2-Hydroxy-3-(2-carboxyphenylthio)-3-12-(14-phenyltetradecyl)phenyl]propionic acid;

2-Hydroxy-3-(2-carboxyphenylthio)-3-(2-butylphenyl)-propionic acid;

2-Hydroxy-3-(2-carboxyphenylthio)-3-(2-dodecylphenyl)propionic acid; and

2-Hydroxy-3-(2-carboxyphenylthio)-3-(2-octadecyl)-propionic acid.

EXAMPLE 2

Preparation of 2(S)-Hydroxy-3(R)-(2-carboxyphenylmethylthio)-3-12-(8-phenyloctyl)phenyl]propionic acid (a) Methyl 3-(2-Carbomethoxyethylthio)-3-12-(8-phenyloctyl)phenyl]-2-hydroxypropionate The compound of Example 1(c) (1.2 g, 3.28 mmol) was dissolved in methanol (20 ml) containing 2% triethylamine and stirred under argon at room temperature. Methyl 3-mercaptopropionate (0.623 ml, 5.45 remoles) and triethylamine (1.45 ml, 9.84 mmol) were dissolved in methanol (15 ml) and added dropwise. The mixture was stirred for 18 hours. The solvent was stripped and the residue eluted with 20% ethyl acetate/hexane to give a mixture of the desired product and its regioisomer, methyl 2-(2-carbomethoxyethylthio)-3-[2-(8-phenyloctyl)phenyl]-3- hydroxypropionate. The mixture was rechromatographed on 100 g of neutral alumina to separate the desired product.

(b) Erythro-3-(2-carboxyethylthio)-3-12-(8-phenyloctyl)phenyl]-2-hydroxypropionic acid The desired product of Example 2(a) (320 mg, 0.66 mmol) was dissolved in methanol (10 ml) and stirred under argon at ice bath temperature. A 1N solution of sodium hydroxide (2.5 ml, 2.5 mmol) was added dropwise, the ice bath removed, the mixture stirred at room temperature for 2.5 hours, and then cooled for 18 hours. After an additional 1 hour of stirring at room temperature, the methanol was stripped, the residue diluted with water and the pH adjusted to 3.5 with dilute hydrochloric acid. Extraction with ethyl acetate followed by drying over anhydrous sodium sulfate, filtration and evaporation gave the crude product which was flash chromatographed on 20 grams of silica gel eluted with 30:70:0.5 ethyl acetate:hexane:formic acid to give the free acid product.

(c) Resolution of 3-(2-carboxyethylthio)-3-12-(8-phenyloctyl)phenyl]-2-hydroxypropionic acid The racemic diacid of Example 2(b) (63.5 g, 0.138 mol) in 700 ml of isopropanol was treated with a solution of (R)-4-bromo-α-phenethylamine (57.1 g, 0.286 mol) in 200 ml of isopropanol at 25° C. The resulting solution was stirred for 3 hours, causing crystallization of the 2S,3R dismine salt. The suspension was cooled to 5° C., filtered, and the salt recrystallized twice from ethanol to give 37.7 q (72%) of 2S,3R dismine salt, m.p. 146°-147° C.; $[\alpha]^{24^\circ C.} = -15.8$, (C=1, $CH_3OH$).

The dismine salt (37.7 g, 0.0497 mol) was added in portions to 400 ml of cold 0.5N aqueous hydrochloric acid. The mixture was extracted with ethyl acetate, and the ethyl acetate solution washed three times with 0.5N hydrochloric acid. The ethyl acetate solution was washed with saturated sodium chloride solution, dried, and concentrated to give 19.5 g (97%) of the desired 2(S)-hydroxy-3(R)-(2-carboxyethylthio)-3-12-(8-phenyloctyl)phenyl]-propionic acid; $[\alpha]^{24^\circ} = =40.8^\circ$ (C=1, $CHCl_3$).

(d) Methyl 2(S)-hydroxy-3(R)-(2-carbomethoxyethylthio)-3-[2-(8@henyloctyl)phenyl]propionate A solution of 2(S)-hydroxy-3(R)-(2-carboxyethylthio)-3-[2-(8-phenyloctyl)phenyl]propionic acid (1.0g, 2.18 mmol) in 100 ml of diethylether was treated with an ethereal solution of diazomethane for 30 minutes at room temperature. Evaporation of the ether gave methyl-2(S)-hydroxy-3(R)-(2-carbomethoxyethylthio)-3-12-(8-phenyloctyl)phenyl]propionate, 1.06 q (100%).

(e) Methyl 2(S)-Hydroxy-3(R)-(carbomethoxyphenylmethylthio)-3-[2-(8-phenyloctyl)phenyl]propionate A solution of the compound of Example 2(d) (675 mg, 1.39 mmol) in 12 ml of tetrahydrofuran and 4 ml of N,N-dimethylformamide at 01 was treated with sodium hydride (2.92 mmol). After 30 min, 2-carbomethoxybenzyl bromide (350 mg, 1.53 mmol) was added and the mixture stirred at 221 for 2 hours and 601 for 2 hours. After cooling, the mixture was diluted with water, acidified, and extracted with ethyl acetate. The extracts were dried and the solvent evaporated. The residue was chromatographed first over silica gel with ethyl acetate/hexane (3:7) as eluant, then over an alumina column with ethyl acetate/hexane/methanol (75:25:1) as eluant. The product was isolated as an oil, 230 mg.

(f) 2(S)-Hydroxy-3(R)-(3-carboxyphenylmethylthio)-3-[2-(8-phenyloctyl) phenyl]propionic acid A solution of the compound of Example 2(e) (130 mg, 0.24 mmol) in 2 ml of methanol was treated with 2 ml of 2.5N sodium hydroxide, and heated at 80, for 10 minutes. The solution was diluted with 10 ml of water, filtered, the filtrate acidified and extracted with ethyl acetate. The extracts were washed with water, dried and the solvent removed to yield the product as an oil, 97 mg (78%). nmr ($CDCl_3/Me_2CO$) 8.05 ppm (d, 1H), 7.67 (m, 1H), 6.96–7.47 (m, 11H), 4.78 (d, 1H), 4.58 (d, 1H), 4.39 (d, 1H), 4.18 (d, 1H), 2.20–2.72 (m, 4H), 1.06–1.72 (m, 12H).

EXAMPLE 3

Preparation of 2(S)-Hydroxy-3(R)-(3-carboxyphenylmethylthio)-3-(2-(8-phenyloctyl)phenyl]propionic acid (a) Methyl 2(S)-hydroxy-3(R)-(3-carboethoxyphenylmethylthio)-3-(2-(8-phenyloctyl) phenyl]propionate A solution of the compound of Example 2(d) (370 mg, 0.76 mmol) in 10 ml of tetrahydrofuran and 5 ml of N,N-dimethylformamide was treated first with sodium hydride (1.53 mmol) followed by 3-carboethoxybenzylbromide (203 mg, 0.84 mmol). The mixture was stirred at 22° for 1 hr, poured into 100 ml of cold 0.1 N hydrochloric acid, and extracted with diethyl ether. The extracts were washed with water, dried, and the drying agent filtered. The filtrate was treated with an ethereal solution of diazomethane for 30 min at 220, then evaporated. The residue was chromatographed initially on alumina with ethyl acetate/hexane/methanol (80:20:5) as eluant, then on silica gel with ethyl acetate/hexane (3:7) as eluant. The product was isolated as an oil, 170 mg (41%).

(b) 2(S)-Hydroxy-3(R)-(3-carboxyphenylmethylthio)-3-(2-(8-phenyloctyl)phenyl]propionic acid A solution of the compound of Example 3(a) (170 mg, 0.30 mmol) in 5 mi of ethanol was treated with 4 ml of 5% sodium hydroxide, and the mixture heated under argon at 651 for 1 hour. The solution was diluted with 10 ml of water, treated with activated charcoal, and filtered. The filtrate was acidified and extracted with chloroform. The extracts were washed with water, dried, and the solvent evaporated, giving the product as an oil, 137 mg (87%). nmr ($CDCl_3$): 7.0–9.0 (m, overlapping broad s, 16H), 4.69 (d, 1H), 4.48 (d, 1H), 3.80 (d, 1H), 3.64 (d, 1H), 2.18–2.70 (m, 4H), 1.0–1.70 (m, 12H).

EXAMPLE 4

Preparation of 2-Hydroxy-3-(3-carboxyphenylthio)-3-[2-(8-phenyloctyl)phenyl]propionic acid (a) Methyl 2@Hydroxy-3-(3-carboxyphenylthio)-3-[2-(8-phenyloctyl)phenyl]propionate A solution of the compound in Example 1(c), (525 mg, 1.4i mmol) and m-mercaptobenzoic acid (331 mg, 2.15 mmol) prepared according to Wiley, P. F., *J. Org. Chem.*, 16, 812 (1951) in a mixture of 4 ml of methanol and 0.5 ml of triethylamine was stirred at 23° for 16 hours. The reaction was poured into 0.5N HCl and extracted with ethyl acetate. The extracts were dried,, evaporated, and the residue chromatographed over silica gel. The product, together with the regioisomeric compound, was eluted with ethyl acetate. The solvent was evaporated, and the residue dissolved in 10 ml of methanol, treated with 1 ml of 25% NaOMe in methanol, and stirred at 23° for 4 hours. The mixture was diluted with 0.5N HCl, and extracted with ethyl acetate. The extracts were dried, evaporated, and the residue chromatographed over silica gel. The product was eluted with a mixture of ethyl acetate, hexane, methanol, and acetic acid (75:25:5:1), and yielded after evaporation of the solvents 185 mg (25%).

(b) 2-Hydroxy-3-(3-carboxyphenylthio)-3-12-(8-phenyloctyl)phenyl]propionic acid

A solution of the compound in Example 4(a) (144 mg, 0.28 mmol) in 5 ml of ethanol was treated with 2 ml of 0.5N NAOH, and stirred at 23° for 2 hours. The reaction was diluted with 10 mi of water, filtered, the filtrate acidified, and extracted with ethyl acetate. The extracts were dried and evaporated and gave the titled product, 105 mg (75%) nmr ($CDCl_3/Me_2CO$):8.22(s,1H), 6.70–8.10(m,15H),5.02(d,J=4.3Hz,1H),4.64(d,J=4.3Hz,1H), 2.42–2.86(m,4H),1.16–1.74(m,12H).

EXAMPLE 5

Preparation of 2-Hydroxy-3-(4-carboxyphenylthio)-3-[2-(8-phenyloctyl)phenyl]propionic acid (a) Methyl 2-hydroxy-3-(4-carbomethoxyphenylthio)-3-[2 - yl)phenyl]propionate A mixture of the compound of Example l(c) (644 mg, 1.76 mmol), and p-mercaptobenzoic acid (325 mg, 2.11 mmol), prepared in a manner similar to the meta analog in Example 4(a), in 10 ml of methanol and 0.6 ml of triethylamine was stirred at 23° for 16 hours. The solution was treated with 1 ml of 25% NaOMe in methanol, stirred 3 hours, poured into 0.5 N hydrochloric acid and extracted with ethyl acetate. The extracts were dried and the solvent evaporated. The residue was esterified with methanol and gaseous HCl, and then chromatographed over silica gel. The product was eluted with a mixture of ethyl acetate and hexane (30:70), and gave 350 mg (37%). nmr $CDCl_3$:4.90(d,1H), 4.50(t,1H).

(b) 2-Hydroxy-3-(4-carboxyphenylthio)-3-[2-(8-phenyloctyl)-phenyl]propionic acid.

The compound of Example 5(a) was hydrolyzed in the same manner as described for the preparation of the compound of Example 4(b), in 48% yield after recrystallization from a mixture of benzene and hexane. nmr($CDCl_3/Me_2CO$):8.00(d,2H), 7.00–7.88(m,14H), 5.12(d, J=4.3Hz,1H), 4.67(d,J=4.3Hz,1H), 2.40–2.90(m,4H), 1.10–1.76 (M,12H).

EXAMPLE 6

Preparation of 2-Hydroxy-3-(4-carboxy-2-methoxyphenylmethylthio)-3-[2-(8-phenyloctyl)phenyl]propionic acid (a) Methyl 3-methoxy-4-mercaptomethylbenzoate A solution of 7.15 g (0.027 mol) methyl 4-bromomethyl-3-methoxybenzoate in 50 ml of $Me_2CO$ was treated with a solution of 2.1 g (0.028 mol) thiourea in 50 ml $Me_2CO$ and the reaction was stirred for 24 hours. The solid isothiouronium hydrobromide was filtered, washed with diethylether and dried. This salt was dissolved in 50 ml of water, treated with 50 ml 3N NAOH, and the mixture refluxed 3 hours under argon. The clear solution was cooled, acidified, and extracted with diethyl ether. The extracts were dried, and treated with an ethereal solution of diazomethane for 30 minutes. Evaporation of the solvent gave methyl 3-methoxy-4-mercaptomethyl benzoate, 4.2 g (73%).

(b) Methyl 2-hi (4-carbomethoxy-2-methoxyphenylmethylthio)-3-[2-(8-phenyloctyl)phenyl]propionate A solution of the compound in Example i(c) (980 mg, 2.68 mmol) and methyl 4-mercaptomethyl-3-methoxy benzoate (625 mg, 2.95 mmol) in 10 ml of methanol and 2 mi of triethylamine were stirred for 16 hours at 23° and then, evaporated. The residue was dissolved in diethyl ether, and washed with 0.5 N HCl. The diethylether layer was dried, and the solvent removed. The residue was dissolved in 15 ml of methanol, treated with 1 ml of 25% NaOMe in methanol, stirred at 23° for 2 hours, and poured into 0.5 N HCl. The mixture was extracted with diethyl ether. The extracts were washed with water, dried and evaporated. The residue was chromatographed over silica gel. The product was eluted with a mixture of ethyl acetate and hexane (25:75), and gave 580 mg (38%). nmr($CDCl_3$): 4.70(t,J=5.1Hz,1H), 4.50(d,J=5.1Hz,1H).

(c) 2-Hydroxy-3-(4-carboxy-2 methoxyphenylmethylthio)-3-1-2-(8-phenyloctyl)phenyl]propionic acid The compound of Example 6(b) was hydrolyzed in the same manner as described for the preparation of the compound in Example 4(b), in 28% yield after trituration with a mixture of benzene and hexane. nmr($CDCl_3/D_2O$): 6.90–7.72(m,12H), 4.70(d,J=4.2Hz,1H), 4.52(d,J=4.2Hz,1H), 3.34–3.95(m,2H), 3.80(s,3H), 2.20–2.68(m,4H), 0.98–1.68(m, 12H).

In a similar manner the following was prepared: 2-hydroxy-3-(5-carboxy-2-methoxy-phenylmethylthio)-3-(2-(8-phenyloctyl)phenyl]propionic acid. nmr ($CDCl_3$): 8.10(d,1H), 7.90(d,2H), 7.50(m, 1H), 6.88–7.22(m, 6H), 6.80(d,2H), 4.76(d, 1H), 4.48(d, 1H), 3.81(s, 3H), 3.70 (d,2H), 2.00–2.60 (m, 4H), 0.67–1.62(m, 12H).

EXAMPLE 7

Preparation of 2-Hydroxy-3-(4-carboxyphenylmethylthio)-3-[2-(8-phenyloctyl)phenyl]propionic acid (a) Methyl-2-hydroxy-3-(4-carbomethoxyphenylmethylthio)-3-(2-(8-phenyloctyl)phenyl]propionate A solution of the compound in Example i(c), (880 mg, 2.40 mmol), and methyl p-mercaptomethylbenzoate (525 mg, 2.88 mmol), prepared similarly to the starting material of Example 6(a), in 10 ml of methanol and 0.4 ml of triethylamine was stirred at 23° for 2 days. 1 ml of 25% NaOMe in methanol was added, stirring was continued 45 minutes, and the reaction was poured into 0.5 N HCl and extracted with methylene chloride. The extracts were dried and the solvents evaporated. The residue was chromatographed over a deactivated alumina column (25 ml $H_2O$/500 gm $Al_2O_3$). Impurities were removed with a mixture of ethyl acetate and hexane (1:4) and the product eluted with a mixture of methanol and ethyl acetate (1:19), and gave 620 mg (47%). nmr($CDCl_3$):4.53(t, J-4.5Hz,1H), 4.40(d,J=4.5Hz,1H).

(b) 2-Hydroxy-3-(4-carboxyphenylmethylthio)-3-[2-(8-phenyloctyl)phenyl]propionic acid The compound of Example 7(a) was hydrolyzed in the same manner as described for the preparation of the compound in Example 4(b), in 46% yield after recrystallization from toluene. nmr($CDCl_3/Me_2CO$): 8.1–9.9(-broad,3H), 8.02(d,J=7.2HZ,2H), 7.67(m,1H), 7.42(d,J=7.2Hz,2H), 6.90–7.28(m,8H), 4.72(d,J=4.2Hz,1H), 4.50(d,J=4.2Hz,1H), 3.92(d,J=13Hz,1H), 3.70(d,J=13Hz,1H), 2.26–2.70(m,4H), 1.02–1.76(m,12H).

EXAMPLE 8

Preparation of 2-Hydroxy-3-(2-fluora-4-carboxyphenylmethylthio)-3-[2-(8-phenyloctyl)phenyl]propionic acid (a) Methyl 2-hydroxy-3-(2-fluoro-4-carbomethoxyphenylmethylthio)-3-[2-(8-phenyloctyl)phenyl]propionate The compound of Example i(c) was reacted with methyl 2-fluoro-4-mercaptomethylbenzoate, prepared in a manner similar to the starting material in Example 6(a), in an analogous manner to that described for the preparation of the compound described in Example 6(b), and gave the product in 22% yield. nmr($CDCl_3$):4.63(t,J=4.9Hz,1H), 4.50(d,J=4.9Hz,1H).

(b) 2-Hydroxy-3-(2-fluoro-4-carboxyphenylmethylthio)-3-(2-(8-phenyloctyl)phenyl]propionic acid The compound of Example 8(a) was hydrolyzed as described for the preparation of the compound described in Example 4(b). nmr($CDCl_3$):6.98–7-90(m,15H), 4.68(d, J=4.6Hz,1H), 4.55(d,J=4.6Hz,1H), 3.80(t,2H), 2.25–2.70(m, 4H), 1.00–1.73(m,12H).

EXAMPLE 9

Preparation of 2-Methoxy-3-(4-carboxyphenylthio)-3-[2-(8-phenyloctyl)phenyl]propionic acid (a) Methyl 2 -methoxy-3-(4-carbomethoxyphenylthio)-3-[2-(8-phenyloctyl)phenyl]propionate A solution of the compound in Example 5(a) (220 mg, 0.4 mmol) in 5 ml of tetrahydrofuran and 1 ml of dimethylformamide at 0° was treated with a 60% dispersion of sodium hydride in mineral oil (16 mg, 0.4 mmol). After 30 minutes, the solution was treated with iodomethane (58 mg, 0.4 mmol), stirring was continued at 23° for 1.5 hours, the reaction was poured into 0.5 N HCl and extracted with diethyl ether. The extracts were dried and evaporated. The residue was chromatographed initially over alumina and eluted with a mixture of ethyl acetate and hexane (35:65). The residue after evaporation of the solvents was chromatographed over a silica gel column. The product was eluted with a mixture of ethyl acetate and hexane (1:3), and gave 97 mg (44%). nmr($CDCl_3$) 4.90(d,J=7.5Hz,1H), 4.12(d,J=7.5Hz,1H), 3.82(s,3H), 3.58(s, 3H), 3.24(s,3H).

(b) 2-Methoxy-3-phenyl 2-(8-phenyloctyl)phenyl]-propionic acid

The compound of Example 9(a) was hydrolyzed in the same manner as described for the preparation of the compound in Example 4(b), in 64% yield after trituration with a mixture of cyclohexane and hexane. nmr($CDCl_3$): 11.28(broad s,2H), 7.82(d,2H), 7.02–7.58(m,11H), 5.10(d,J=9.6Hz,1H), 4.26(d,J=9.6Hz,1H), 3.20(s,3H), 2.45–2.98(m,4H), 1.18–1.90(m,12H).

In a similar manner the following was prepared:

2-methoxy-3-(4-carboxy-2-methoxyphenylmethylthio)-3-[2-(8-phenyloctyl)phenyl]propionic acid;

2-Methoxy-3-(4-carboxyphenylthio)-3[2-(3-phenylpropyl)phenyl]propionic acid; and 2-Methoxy-3-(4-carboxy-2-methoxyphenylmethylthio)-3-[2-(14-phenyltetradecyl)phenyl]propionic acid.

EXAMPLE 10

Preparation of 2-Hydroxy-3-(4-hydroxyphenylthio)-3-[2-(8-phenyloctyl)phenyl]propionic acid (a) Methyl 2-hydroxy-3-(4-hydroxyphenylthio)-3-[2-(8-phenyloctyl)phenyl]propionate The compound of Example 1(c) (722 mg, 2 mmol) was dissolved in methanol (10 ml) containing 2% triethylamine and the solution was stirred under argon at room temperature. Triethylamine (1.68 ml, 12 mmol), and 4-hydroxythiophenol (428 mg, 3.4 mmol) were dissolved in methanol (15 ml) and added to the reaction mixture which was then stirred overnight at room temperature. The solvent was evaporated and the residue was flash chromatographed on 80 grams of silica gel eluted with 30% ethyl acetate/hexane to give a mixture of the desired product and its regioisomer, methyl 3-hydroxy-2-(4-hydroxyphenylthio)-3[2-(8-phenyloctyl)-phenyl]propionate. The mixture of regioisomers was dissolved in methanol (20 ml) and stirred under argon at room temperature. Sodium methoxide, 25 wt. % in methanol, (0-92 ml, 4 mmol) was added dropwise and the mixture-stirred for 2.5 hours. The mixture was cooled in an ice bath and acetic acid (0.3 ml, 5.2 mmol) was added dropwise. The solvent was evaporated and the residue was partitioned between ethyl acetate and water. The organic phase was dried over anhydrous sodium sulfate, filtered and evaporated to give the crude product which was flash chromatographed on 80 grams of silica gel eluted with 25% ethyl acetate/hexane to give the desired product.

(b) 2-Hydroxy-3-(4-hydroxyphenylthio)-3-[2-(8-phenyloctyl)phenyl]propionic acid

The compound of example 10(a) (410 mg, 0.83 mmol) was dissolved in methanol (10 ml) and stirred under argon at ice bath temperature. A 1N solution of sodium hydroxide (4 ml, 4 mmol) was added and the mixture stirred overnight at room temperature. The solvent was evaporated and the residue was acidified with dilute hydrochloric acid. Extraction with ethyl acetate followed by drying the organic phase over anhydrous sodium sulfate, filtration and evaporation gave the crude product which was recrystallized from ethyl acetate/hexane to give the desired product as a white crystalline solid, m.p. 155°-157° C. Analysis for $C_{29}H_{34}O_4S$: Calculated: C,72.77; H,7.16; S, 6.70. Found: C, 72.90; H, 6.91; S,6.95.

EXAMPLE 11

Preparation of 2-Methoxy-3-(4-carboxy-2-methoxyphenylmethylthio)-3-(2-(8-phenyloctl]propionic acid (a) Methyl 2-methoxy-3-(4-carbomethoxy-2-methoxyphenylmethylthio)-3-[2-(8-phenyloctyl)phenyl]propionate The compound of Example 6(b) was reacted in the same manner as for the preparation of the compound of Example 9(a), and gave the product in 53% yield. nmr ($CDCl_3$): 4.48(d,J=7.2Hz, 1H), 4.15(d.J=7.2Hz, 1H), 3.90 (s,3H), 3.85(s,3H), 3.72(s, 3H), 3.33(s,3H).

(b) 2-Methoxy- -carboxy-2-methoxyphenylmethylthio)-3-[2-(8-phenyloctyl)phenyl]propionic acid The compound of Example 11(a) was hydrolyzed as described for the preparation of the compound described in Example 4(b) to yield the desired product. nmr ($CDCl_3$): 4.52(d,J=6.3Hz,1H), 4.18(d, J=6.3Hz,1H), 3.86(s, 3H), 3.42(s, 3H).

EXAMPLE 12

Preparation of 3-(4-Carboxy-2-methoxyphenylmethylthio)-3-[2-(8-phenyloctyl)phenyl]propionic acid A solution of 0.54 g (1.32 mmol) of tert-butyl 3-hydroxy-3-[2-(8-phenyloctyl)phenyl]propionate and 0.52 gm, (2.64 mmol) of 3-methoxy-4-mercaptomethylbenzoic acid in 10 ml of methylene chloride at 0° was treated dropwise with 20 ml of trifluoroacetic acid. Stirring was continued at 0° for 4 hours and 221 for 1 hour, and all the solvents were thoroughly evaporated. The residue was crystallized first from $H_2O$/MECN (1:4), and then from $Me_2CO$/hexane, and to yield the product, 0.26 gm. nmr ($CDCl_3/Me_2CO/DMSO$): 7.05-7.72(m, 12H), 4.52 (d of d, 1H), 4.83(d, 1H), 4.82(s,3H), 4.68(d.1H), 2.88-3.24(m, 2H), 2.36-2.74 (m, 4H), 1.10-1.75(m,12H).

EXAMPLE 13

Preparation of Methyl 2-hydroxy-3-mercapto-3-[2-(8-phenyloctyl)phenyl]propionate (a) Methyl 2-hydroxy-3-(4-methoxyphenylmethylthio)-3-[2-(8-phenyloctyl)phenyl]propionate A solution of 4.54 gm (12.4 mmol) of the epoxyester of Example i(c) and 1.91 gm.(12.4 mmol) of p-methoxybenzyl mercaptan in a mixture of 1.7 ml of triethylamine and 20 ml of methanol were stirred for 42 hours, and the solvents evaporated. The residue was dissolved in diethyl ether and washed with 0.1 N HCl. The organic layer was dried, and the solvent evaporated. The residue was chromatographed over an alumina column. Impurities and the undesired regioisomer were eluted with hexane/ethyl acetate/reethanol (60:40:1). The desired product was eluted with hexane/ethyl acetate/-methanol (40:60:2), 2.6 gm (40%). nmr ($CDCl_3$): 7.68(m, 1H), 7.20(m, 10H), 6.82(d, 2H), 4.58(t,1H), 4.45 (d, 1H), 3.82 (s, 3H), 3.72 (s, 2H), 2.66(s, 3H), 3.14(d, 1H), 2.24-2.72 (m, 4H), 1.10-1.72 (m, 12H).

(b) Methyl 2-hydroxy-3-mercapto-3-(2-(8-phenyloctyl)phenyl]propionate

A solution of 1.1 gm (2.12 mmol) of the compound in Example 13(a) in 25 ml of methanol was treated with a solution of 2.02 gm (6.35 mmol) of mercuric acetate in 100 ml of methanol. After stirring 16 hours, the white precipitate was filtered and washed with diethyl ether. This mercuric salt was dissolved in 25 ml of hot dimethylformamide, 50 ml of methanol was added, and $H_2S$ was bubbled into the solution for 30 minutes. The black precipitate was filtered, the filtrate was concentrated, diluted with water, and extracted with diethyl ether. The diethyl ether layer was washed well with water, dried, and the solvent evaporated. The residue was chromatographed over a silica gel column, and the product was eluted with a mixture of ethyl acetate /hexane (40:60), 370 mg (44%). nmr ($CDCl_3/D_2O$): 7.02-7.78 (m, 9H), 4.62 (s, 2 ), 3.70 (s, 3H), 2.50-2-88 (m, 4H), 1.20-1-82 (m, 12H).

EXAMPLE 14

Preparation of 2-Hydroxy-3-(2-undecyloxyphenyl)-3-(3-carboxyphenylthio)propionic acid (a) 2-Undecyloxybenzaldehyde To a stirred suspension of sodium hydride (10.0 mmol), which was prewashed with petroleum ether, in sieve dried dimethylformamide (10 ml) was-added dropwise a solution of salicylaldehyde (10.1 mmol) in dimethylformamide (1 ml). To the reaction mixture was then added undecyl bromide (10.0 mmol) and the mixture stirred for 16 hours at ambient temperature under nitrogen. The reaction mixture was taken up in hexane (50 ml) and washed with 10 percent sodium hydroxide (2×50 ml) and saturated sodium chloride (50 ml). The organic phase was dried over anhydrous magnesium sulfate and charcoal. Evaporation of the volatiles yielded a colorless liquid which was purified by flash chromatography over silica gel with 2 percent ethyl acetate in hexane as eluant to afford the desired product as an oil.

Analysis for $C_{18}H_2O_2$: Calculated: C, 78.21; H, 10.21. Found: C, 77.92; H, 9.95.

b) 2-Hydroxy-3-(2-undecylo -3-(3-carboxyphenylthio)propionic acid

Employing the general methods of Example 1(c)–1(e), the compound of Example 14(a) is converted to the desired product.

The following compounds are prepared according to the general methods of Example 1(c)–1(e) from the appropriate alkyloxybenzaldehyde which is prepared by the general procedure of Example 14(a) from salicylaldehyde or 2-mercaptobenzaldehyde and the appropriate alkyl halide;

- 2-Hydroxy-3-(2-heptyloxyphenyl)-3-(3-carboxyphenylthio)propionic acid;
- 2-Hydroxy-3-(2-dodecyloxyphenyl)-3-(3-carboxyphenylthio)propionic acid.
- 2-Hydroxy-3-(5-methoxy-2-dodecyloxyphenyl)-3-(3-carboxyphenylthio)propionic acid;
- 2-Hydroxy-3-(5-methyl-2-dodecyloxyphenyl)-3-(3-carboxyphenylthio)propionic acid;
- 2-Hydroxy-3-(5-fluoro-2-dodecyloxyphenyl)-3-(3-carboxyphenylthio)propionic acid;
- 2-Hydroxy-3-(5-chloro-2-dodecyloxyphenyl)-3-(3-carboxyphenylthio)propionic acid;
- 2-Hydroxy-3-(5-iodo-2-dodecyloxyphenyl)-3-(3-carboxyphenylthio)propionic acid;
- 2-Hydroxy-3-(5-bromo-2-dodecyloxyphenyl)-3-(3-carboxyphenylthio)propionic acid;
- 2-Hydroxy-3-(5-hydroxy-2-dodecyloxyphenyl)-3-(3-carboxyphenylthio)propionic acid;
- 2-Hydroxy-3-(5-nitro-2-dodecyloxyphenyl)-3-(3-carboxyphenylthio)propionic acid;
- 2-Hydroxy-3-(5-amino-2-dodecyloxyphenyl)-3-(3-carboxyphenylthio)propionic acid.
- 2-Hydroxy-3-(5-trifluoromethyl-2-dodecyloxyphenyl)-3-(3-carboxyphenylthio)propionic acid;
- 2-Hydroxy-3-(2-dodecylthiophenyl-3-(3-carboxyphenylthio)propionic acid is prepared from 2-(dodecylthio)benzaldehyde.
- 2-Hydroxy-3-(2-heptylthiophenyl)-3-(3-carboxyphenylthio)propionic acid is prepared from 2-(heptylthio)-benzaldehyde.

EXAMPLE 15

Preparation of 2-Hydroxy-3-(2-6-phenylhexyloxy)phenyl]-3-(3-carboxyphenylthio)propionic acid a) 2-(6-Phenylhexyloxy)benzaldehyde A solution of 6-phenylhexanoic acid (19.8 mmol) in sieve dried tetrahydrofuran (5 ml) was reduced with diborane in tetrahydrofuran (30 ml, 29.1 mmol) at 0° C. for 4 hours to give 6-phenylhexanol. To an ice cold solution of the hexanol (ca. 19.8 mmol) and carbon tetrabromide (21.98 mmol) in methylene chloride (50 ml) was added triphenylphosphine (22–30 mmol) in methylene chloride (50 ml) and the resulting solution was stirred for 2.5 hours. The volatiles were evaporated and the residue was taken up in ether (100 ml), cooled in ice, and filtered. The filtrate was evaporated and distilled to afford 6-phenylhexyl bromide as an oil. A mixture of the bromide (8.00 mmol), salicylaldehyde (8.19 mmol) and potassium carbonate (9.33 mmol) in dimethylformamide (10 ml) was heated to 100° C. and maintained at that temperature for one hour. The cooled reaction mixture was taken up in hexane (50 ml) and washed with 5% sodium hydroxide (50 ml) and saturated sodium chloride (50 ml). The organic phase was dried over anhydrous magnesium sulfate and charcoal. Evaporated yielded a colorless oil which was purified by flash chromatography over silica gel with 5% ethyl acetate in hexane as eluant to afford the desired product as an oil.

Analysis for $C_{19}H_2O_2$: Calculated: C, 80.82; H, 7.85. Found: C, 80.62; H, 7.72.

(b) 2-Hydroxy-3–12-(6-phenylhexyloxy)phenyl]-3-(3-carboxyphenylthio)propionic acid Employing the general methods of Example 1(c) through 1(e) the compound of Example 15(a) is converted to the desired product.

The following compounds are prepared according to the general methods described above from the appropriately substituted phenylalkyloxybenzaldehyde.

- 2-Hydroxy-3–12-(3-phenylpropyloxy)phenyl]-3-(3-carboxyphenylthio)propionic acid; and
- 2-Hydroxy-3–12-(9-phenylnonyloxy)phenyl]-3-(3-carboxyphenylthio)propionic acid.

EXAMPLE 16

Preparation of 3-[2-(6-phenylthiohexylthio)phenyl]-3-(2-carboxyphenylthio)-2-hydroxypropionic acid a) Preparation of 2-(6-thiophenoxyhexylthio)benzoic acid Thiosalicylic acid (1.2 g, 0.008 mole) and 6-thiophenoxyhexylbromide (2.5 g, 0.009 mole) are dissolved in dimethylformamide (50 ml) and the solution is stirred under argon. Potassium carbonate (1.5 g, 0.011 mole) is added carefully to the reaction. After the addition is complete the mixture is slowly warmed to 100° C. The solvents are evaporated, and the residue is dissolved in water, acidified with dilute hydrochloric acid, extracted with ethyl acetate, dried over anhydrous sodium sulfate, filtered, and evaporated. The residue is flash chromatographed on silica gel to give the desired product.

b) Preparation of 2-(6-phenylthiohexylthio)benzyl alcohol

To a suspension of lithium aluminum hydride (0.292 g, 0.007 mole) in tetrahydrofuran (30 ml) is added a solution of 2-(6-thiophenoxyhexylthio)benzoic acid (2.42 g, 0.007 mole) in tetrahydrofuran (30 ml). The reaction is stirred at room temperature under argon, overnight. When the reaction is complete several drops of ice water are added followed by cold 10% sodium hydroxide (approximately 1.0 ml), followed by cold 10% sodium hydroxide (approximately 1.0 ml), followed by more ice water. This produces a dry granular precipatate which is filtered and is washed. The filtrate is then dried over magnesium sulfate, filtered and is evaporated. The crude alcohol is flash chromatographed on silica gel to give the desired compound.

c) Preparation 2-(6-phenylthiohexylthio)benzaldehyde

To a suspension of manganese dioxide (11.78 g, 0.135 mole) in ethyl acetate (30 ml) is added a solution of 2-(6-thiophenoxyhexylthio)benzyl alcohol (1.23 g; 0.0037 mole) in ethyl acetate (20 ml). The reaction is stirred at room temperature under argon for 1.5 hours. The suspension is then filtered. The filtrate is dried over magnesium sulfate, filtered and evaporated providing the desired compound.

d) Methyl trans-3-[2-(6-phenylthiohexylthio)phenyl]-2,3-epoxypropionate

The compound of Example 16(c) (10 mmol) is dissolved in diethyl ether (25 ml) and the solution is stirred under argon at 0° C. Methyl chloroacetate (15 mmol) is added followed by the addition of sodium methoxide (15 mmol). The mixture is stirred for 2.5 hours at ice bath temperature. A small quantity of water is added, the ether phase is separated, dried over anhydrous sodium sulfate, filtered, and evaporated. The residue is flash chromatographed on 80 grams of silica gel eluted with 5-30% ethyl acetate/hexane to give the product.

(e) Methyl 3-12-(6-phenylthiohexylthio)phenyl]-3-(2-carboxyphenylthio)-2-hydroxypropionate A solution of the compound of Example 16(d) (1.39 mmol), 2-mercaptobenzoic acid (1-53 mmol) and triethylamine (3.06 mmol) in 10 ml of methanol are stirred overnight at 22° under argon. The mixture is poured into water, acidified with 1N hydrochloric acid, and is extracted with diethylether. The extracts are dried and the solvent evaporated. The residue is chromatographed on silica gel to remove starting materials and the product is eluted with a mixture of ethyl acetate, hexane, and methanol (60:40:2.5). The solvents are evaporated, and the residue is recrystallized from methanol to yield the product.

f) 3-[2-(6-phenylthiohexylthio)phenyl]-3-(2-carboxyphenylthio)-2-hydroxypropionic acid A suspension of the compound of Example 16(e) (0.44 mmol), 5 ml of methanol, 2 ml of water and 2.5N sodium hydroxide is heated at 95° for 10 minutes, and is stirred at 22° for 2 hours. The mixture is diluted with 20 ml of water and filtered. The filtrate is acidified, and extracted with ethyl acetate. The extracts are washed with water, dried, and the solvent evaporated. The residue is recrystallized from acetonitrile to give the desired product.

EXAMPLE 17

Preparation of 2-Hydroxy-3-(2-carboxy-4-oxo-8-propyl-4H-1-benzopyran-7-ylthio)-3-12-(8-phenyloctyl)phenyl]propionic acid (a) Ethyl 7-((dimethylamino)thioxomethoxy)-4-oxo-8-propyl-4H-1-benzopyran-2-carboxylate Ethyl 7-hydroxy-4-oxo-8-n-propyl-4H-1-benzopyran-2-carboxylate (1 g) in anhydrous dimethylformamide (4 ml) is cooled to 0° and treated under nitrogen with sodium hydride (50% dispersion in mineral oil, 180 mg) with stirring for 30 minutes. Dimethylaminothiocarbamylchloride (465 mg) is added and the mixture is stirred 15 minutes at 0°, warmed to 80° and maintained as such for 18 hours. The mixture is cooled, diluted with methylene chloride (50 ml) and washed with water (3×100 ml)), dried over sodium sulfate and reduced to dryness in vacuo. The residue is recrystallized from ethyl acetate and hexane to yield the title compound.

(b) Ethyl 7-(((dimethylamino)carbonyl)thio)-4-oxo-8-propyl-4H-1-benzopyran-2-carboxylate The ester prepared in Example 17(a) is heated neat under a nitrogen atmosphere at 200° for 2 hours. After cooling the residue is crystallized from ethyl acetate and hexane to yield the title compound.

(c) 7-Mercapto-4-oxo-8-propyl-4H-1-benzopyran-2-carboxylic acid

Sodium (690 mg) is dissolved in anhydrous methanol (50 ml) and to this is added the compound of Example 17(b). The mixture is stirred under a nitrogen atmosphere for 3 hours at ambient temperature. Water (50 ml) is added and the mixture is acidified with 6N HCl. The resulting crystals are collected by filtration and recrystallized from ethyl acetate to provide the title compound.

(d) Methyl 2-hydroxy-3-(2-carboxy-4-oxo-8-propyl-4H-benzopyran-7-yl thio)-3-[2-(8-phenyloctyl)phenyl]-propionate The compound of Example 1(c), methyl trans-3-[2-(8-phenyloctyl)phenyl]-2,3-epoxypropionate, is reacted with the 7-mercapto-4-oxo-8-propyl-4H-1-benzopyran-2-carboxylic acid of Example 17(c) in an analagous manner to that for the preparation of the compound in Example 1(d) to yield the desired product.

(e) 2-Hydroxy-3-(2-carboxy-4-oxo-8-propyl-4H-1-benzopyran-7-yl thio)-3-[2-(8-phenyloctyl)phenyl]propionic acid.

The compound from Example 18(d) is hydrolyzed with aqueous NAOH in an analagous manner to that for the preparation of the compound in Example 1(e) to yield to desired product.

EXAMPLE 18

Preparation of 2-Hydroxy-3-1(5-carboxy-2-methoxyphenylmethyl)thiol-3-[2-(8-phenyloctylphenyl]propionic acid (a) Methyl 2-hydroxy-3-((5-carbomethoxy-2-methoxyphenylmethyl)thiol-3[2-(8-phenyloctyl)phenyl]propionate This compound was prepared from the compound of Example 1(c) in a manner analogous to the preparation of the compound of Example 6(b).

nmr($CDCl_3$): 7.97(m,2H), 7.61(m,1H), 7.04-7.42 (m,8H), 6.87(d,1H), 4.71(t,1H), 4.519d,1H), 3.92(s,3h), 3.88(s,3H), 3.80(m, 2H), 3.64(s,3H), 3.20(d,1H), 2.60(5,2H), 2.42(m,2H), 1.12-1.83(m,12H).

(b) 2-Hydroxy-3-[(5-carboxy-2-methoxyphenylmethyl)thio]-3-[2-(8-phenyloctyl)phenyl]propionic acid The compound of Example 18(a) was hydrolyzed in the same manner as described for the preparation of the compound of Example 4(b) after tituration with a mixture of cyclohexane and hexane.

nmr($CDCl_3$): 8.10(d,1H), 7.90(d,1H), 7.52(m,1H), 6.86-7.21(m,8H), 6.89(d,1h), 4.76(d,1H), 4.48(d,1H), 3.5-3.92(m+s,5H), 2.48(t,2H), 1.98-2.38(m,2H), 0.76-1.62(m,12H).

EXAMPLE 19

Preparation of [R-(R*,S*)]-3-[(4-carboxyphenyl)sulfonyl]-2-methoxy-3-[2-(8-phenyloctyl)phenyl]propionic acid (a) (E)-1-(2-napthyl)-3-[2-(8-phenyloctyl)phenyl]-propenone To a 12 L 3-neck flash equipped with vigorous overhead stirring, a condenser and a cool bath (51), under nitrogen flush, sodium metal (36.8 g., 1.16 M) was added to ethanol (3.53 L, 95%) over a period of 30 minutes. After stirring for 4 minutes, 2-phenyloctyl benzaldehyde was added. Upon completion, the reaction was recooled to 10° and the 2-acetonapthone (115.6 g., 0.679 M) was added in one portion. The reaction was stirred at ambient temperature for 18 h, during which time a yellow solid precipitated. The reaction was treated with icewater (350 ml) and cooled to 10°. After stirring for 1 hour, the reaction was filtered and the filter cake was washed with 50% aqueous ethanol (400 ml). The solid was air dried, pulverized and dried in vacuo (1-5 mm at room temperature) to yield 248 g. (89%) of the titled compound.

m.p.: 41-42.5]°

TLC: $R_f$=0.55 (methylene chloride; hexane 3:1,silica gel)

HPLC: RT=17.7 min. (WATERS μbondapake® C-18 RP; acetonitrile: water 85:15; 1.5 ml/min.; UV detection at 230 nm)

IR(nujol mull): 1660, 1595, 1185 $cm^{-1}$

CMR[$CDCl_3$]: δ190.3, 143.3, 142.9, 142.4, 135.6, 133.5 1343.5, 132.6, 130.2, 130.15, 129.9, 129.5, 128.5, 128.3, 128.2, 127.8, 126.7, 126.6, 126.3, 125.5, 124.5, 123.3, 35.9, 33.4, 31.72, 31.4, 29.4, 29.38, 29.34, 29.23

PMR[$CDCl_3$]: δ8.55(s), 8.21(d;J=15.5 Hz), 8.11(d of d), 7.9-8.0(m), 7.8(d), 7.50-7.65(m), 7.1-7.4(m), 2.75(t; J=7.71 Hz), 2.57(5; J=7.71 Hz), 1.6(br. s), 1.29(br. s)

Elemental Analysis: Theory: C, 88.74; H, 7.67; Found: C, 88.84; H, 7.68.

(b)(2R) 1-(2-napthyl)-3-[2-(8-phenyloctyl)phenyl]-trans-2,3-epoxy-propan-1-one

Sodium hydroxide (255 g, 6.37 m) was dissolved in deionized water (0.65 L) which was cooled in a water bath at 14°-20° C. Poly-L-leucine (215 g) was added to this solution as a solid. The chalcone (250 g, .531 M) was added as a solid followed by hexane (4 L). The heterogeneous mixture was stirred at ambient temperature for 16 hours, cooled to 10°-15° C. in an ice bath and ethylenediaminetetraacetic acid, disodium salt dehydrate (5 g) was added. 30% Hydrogen peroxide (1.126 L) was added dropwise over 1-2 hours in such a manner that the reaction temperature did not exceed 25° C. The peroxide was directed below the surface of the reaction by a polypropylene tube attached to a dropping funnel. The reaction was stirred at 20°-24° C. for 20 hours.

The reaction was treated with ethyl acetate (0.3 L) and the reaction mixture was filtered through a jacketed bench Buchner funnel (40°-50° C). The solid, poly-L-leucine, was washed with ethyl acetate (0.5 L), slurried in hot (40°-50° C.) ethyl acetate (1-5 L) for 10 minutes and collected.

The combined filtrates were placed in a separatory funnel and washed with three portions of water (550 ml each) and one portion of brine (i L). The organic layer was dried over magnesium sulfate (300 g) for 5 hours, filtered and evaporated (30°-40C., 15 minutes) to an off-white solid.

The solid was recrystallized by dissolving in hot hexane-toluene (95-5 v/v, 1.9 L) and filtering through a jacketed bench Buchner funnel (40° C.). The solution was left at ambient temperature for 1.5 hours and placed in a refrigerator (at 5° C.) for 12 hours. The crystalline product was collected and washed with a small portion of the filtrate and cold hexane. The product was air dried for 3 hours and further dried in a vacuum dessicator (1 mm, 25° C.) for 24 hours. This procedure yielded 200 g (82%) of the titled compound (96-97% e.e.).

m.p.: 62°-63° C.

TLC: Rf=0.35 ($CHCl_3$)

Rf=0.43 (methylene chloride:hexane 3:1)

HPLC: RT =6.0 min. (Waters μbondapak® C18 RP, 3.9 mm ×30 cm; acetonitrile:water 9:1; 2 ml/min, detection at 211 nm)

RT=12.1 min. (OP(+) 4.5 mm×25 cm; methanol; 0.8 ml/min, detection at 210 nm) enantomer RT =18.8 min. Elemental Analysis: theoretical, C 85.67, H 7.40; found, C 85.93, H 7.48

$[\alpha]_D$ (C=1, $CH_2Cl_2$)+24.6; recryx 1x, $[\alpha]_D$=+26.4, [$\alpha_{546}$ (c=1, $CH_2Cl_2$)=+31.1.

CMR[$CDCl_3$]: δ193.13, 142.89, 141.47, 136.02, 133.56, 133.00, 132.49, 130.47, 129.72, 129.37, 129.06, 128.93, 128.55, 128.39, 128.22, 127.91, 127.12, 126.47, 125.56, 124.31, 123.69, 60.48, 57.67, 35.85, 32.73, 31.18, 29.39, 29.18, 29.10

(c) 2(R) 3-[2-(8-phenyloctyl)phenyl]-trans-2,3-epoxy-propionic acid, 2-napthyl ester Methylene chloride (300 ml) was warmed to reflux and m-chloroperoxybenzoid acid (28 g, 0.162 M; 85% was added followed by the 2(R) 1-(2-napthyl)-2,3-(trans)-epoxy-3-[2-(8-phenyl octyl)phenyl]propanane (29g, 0.162 M). The reaction was stirred at reflux for 4 hours, cooled to 15 C, then m-chlorobenzoic acid was removed by filtration and the solvent was evaporated. The residue was dissolved in hot isopropanol/toluene (1L/0.1L) filtered and allowed to cool at room temperature. Crystals formed within 5 minutes. The mixture was cooled in the refrigerator overnight, filtered, and air dried (25°, 1 mm/Hg) to yield 25 g (81%, 99.9% e.e.) of the titled product.

m.p.: 82°-83° C.

Specific rotation: $\alpha_D$ (c=1, $CH_2Cl_2$)=−89.48;

Elemental Analysis: theoretical, C 82.80, H 7.20; found C 82.92, H 7.09

(d) (2R) 3-(2-(8-phenyloctyl)phenyl)-2,3-(trans)-epoxy propionamide

The ester of Example 19(c) (2.03 g) was dissolved in methanol (21.1 ml) and cooled in an ice bath. Methanol saturated with ammonia (21.1 ml) was added dropwise with a temperature rise to 5° C. After 5 hours the methanol/ammonia was evaporated. The ammonia was chased by solution and evaporation from toluene. The residue was further dissolved in toluene, washed with water (1×), 10% NAOH (3×), water (2×), and brine (1×). After drying over $MgSO_4$, the solution was filtered and the solvent evaporated. The resulting solid was dissolved in hot hexane: $CH_2Cl_2$ (90:10), filtered through a hot jacketed Buchner funnel into a warmed filter flash and allowed to precipitate. After 3½ hours at room temperature, the solid was collected by filtration and dried to yield 1.11 g of the titled compound.

mp. 80°-82° C.

Elemental Analysis: theory, C:78.59, H: 8.32, N: 3.99; found, C: 78.35, H: 8.34, N: 3.90

$[\alpha]_D^{25}$=−8.3 (c=1, $CH_2Cl_2$)

(e) [R-(R*,S*)]-3-[(4-carbomethoxyphenyl)thiol-2-hydroxy-3-[2-(8-phenyloctyl)phenyl]propionamide A solution of 4.9gm (0.014 mole) of the compound of Example 19(d) in 100 ml of THF at 01 was treated with 10.4 ml (0.035 mole) of titanium isopropoxide, and stirred 30 minutes. This was then treated with a solution of 3.5 gm (0.021 mole) of methyl-p-mercaptobenzoate in 50 ml of THF which had been treated with 100 mg of 60% NaH. The combined solution was stirred at 0° for 2 hours, poured into 400 ml of 10%. $H_2SO_4$, and extracted with $Et_2O$. The extracts were washed with $H_2O$ and aqueous $Na_2CO_3$, dried and the solvent removed. The residue was chromatographed over silica gel, and a quantitative recovery of the product was eluted with a mixture of 10% MEOH and 90% EtOAc.

nmr ($CDCl_3$ ):7.93(d,2H), 7.69(m,1H), 7.46(d,2H), 6.98–7.40(m,8H), 6.30(d,1HO, 5.62(d,1H), 5.22(d,1H), 4.42(t,1H), 3.88(s,3H), 2.40–3.02(m,5H), 1.09–1.82(m,12H).

(f) Methyl[R-(R*,S*)]-3-[(4-carbomethoxyphenyl) thiol-2-hydroxy-3-[2-(8-phenyloctyl)phenyl]propionate A solution of 7.6 gm of the compound of Example 19(e) in a mixture of 180ml of MEOH, 15ml of conc. HCl and 10ml. of $H_2O$ was refluxed 16 hours. The MEOH was removed, and the residue extracted with $Et_2O$. The extracts were washed with $H_2O$, dried, and the solvent removed. The residue was chromatographed over a silica gel column, and 6.4 gm (89%) of the product was eluted with a mixture of 40% EtOAc and 60% hexane. nmr($CDCl_3$): 7.94(d,2H), 7.62(m,1H), 7.40(d,2H), 6.97–7.27(m,8H), 4.95(d,1H), 4.54(t,1H), 3.82(s,3H), 3.52(s,3H), 3.13(d,1H), 2.37–2.80(m,4H), 1.03–1.87(m,12H).

(g) Methyl [R-R*,S*)1-3-[(4-carbomethoxyphenyl)-thiol-2-methoxy-3-[2-(8-phenyloctyl)phenyl]propionate A solution of 4.08 gm (7.8 mmole) of the compound of Example 19(f) in a mixture of 80 ml of THF and 20 ml of DMF at 0° was treated first with a slurry of 343mg of 60% NcH (washed free of mineral oil with hexane) in 10 ml. of THF, and then 0.54ml (8.6 mmole) of iodomethane. After 30 minutes, the mixture was poured into 100 ml of cold 0.5N HCl, and extracted with $Et_2O$. The extracts were washed with $H_2O$ and aqueous $NAHSO_3$, dried, and the solvent evaporated. The residue was chromatographed over a silica gel column, and 3.19 gm (76%) of the product was eluted with $CHCL_3$.

nmr($CDCl_3$); 7.92(d,2H), 7.00–7.60(m,11H), 4.93(d,1H), 4.18(d,1H), 3.90(s,3H), 3.61(s,3H), 3.33(s,3H), 2.47–2.80(m,4H) 1.17–1.80(m 12H).

(h) Methyl [R-(R*,S*)1-3-[4-carbomethoxyphenyl)-sulfonyl]-2-methoxy-3-[2-(8-phenyloctyl)phenyl]propionate A solution of 1.26 gm (2.3 mmole) of the compound of Example 19(g) in 100 ml of $CH_2Cl_2$ was treated with a solution of 1.25 gm of 80% m-chloroperbenzoic acid in 100 ml of $CH_2Cl_2$. The reaction was stirred at 23° for 1 hour, then washed twice with aqueous $Na_2CO_3$, once with aqueous $NAHSO_3$, then dried and the solvent evaporated. The residue was chromatographed over a silica gel column, and 1.22 gm (95%) of product was eluted with $CHCl_3$ nmr($CDCl_3$): 8.03(d,2H), 7.53(broad d,3H), 6.87–7.43(m,8H), 5.10(d,1H), 4.90(d,1H), 3.93(s,3H), 3.68(s,3H), 3.52(s,3H), 2.03–2.80(m,6H), 1.00–1.86(m,10H).

(i) (R-(R*,S*)1-3-[(4-Carboxyphenyl)sulfonyl]-2-methoxy-3-[2-(8-phenyloctyl)phenyl]propionic acid A solution of 1.22 gm of the compound of Example 19(h) in a mixture of 6 ml of glacial HOAC and 3 ml of conc. HCl was refluxed 9.5 hours, cooled, and poured into 150 ml of $CHCl_3$. This solution was washed twice with $H_2O$, dried, and the solvent evaporated, and gave 0.97 gm of product.

nmr ($CDCl_3$): 8.03(d,2H), 7.53(broad d, 3H), 6.80–7.40(m,8H), 5.17(d,1H), 4.96(d,1H), 3.60(s,3H), 2.60(t,2H), 2.10–2.70(m,2H), 0.93–1.77(m,12H).

EXAMPLE 20

Preparation of [R(R*,S*)1-3-[(4-Carboxyphenyl)thiol-2-methoxy-3-[2-(8-phenyloctyl)phenyl]propionic acid A solution of 177 mg of the compound of Example 19 (g) in 10 ml of MEOH was treated with 2ml of 2.5N NAOH and stirred 16 hours at 23°. The solution was poured into 50 ml of $H_2O$, and filtered. The filtrate was acidified and extracted with $CH_2Cl_2$. The extracts were washed with $H_2O$, dried and the solvent evaporated, and gave the product, 120 g.

nmr($CDCl_3$):7.82(d,2H), 7.58(d,2H), 7.02–7.58(m,9H), 5.10(d,1H), 4.26(d,1H), 3.20(s,3H), 2.98(m,2H), 2.45(t,2H), 1.18–1.90(m,12H).

EXAMPLE 21

Preparation of [R-(R*,S*)]-3-[(4-Carboxyphenyl) thiol-2-hydroxy-3-[2-(8-phenyloctyl)phenyl]propionic acid This compound was prepared from the compound of Example 19(g) in exactly the same manner as used in Example 20.

nmr:($CDCl_3$/$Me_2CO$):8.00(d,2H), 7.70(m,1H), 7.49(d,2H), 7.00–7.45(m,8H), 5.12(d,1H), 4.67(d,1H), 2.40–2.90(m,4H), 1.10–1.76(n,12H).

EXAMPLE 22

Preparation of (R-(R*, S*)]-3-[(4-carboxy-2-methoxyphenylmethyl)thio]-2-hydroxy-3-[2-(8-phenyloctyl)phenyl]propionic acid (a) [R-(R*,S*)]-3-[(4-carbomethoxy-2-methoxyphenylmethylthiol-2-hydroxy-3-[2-(8-phenyloctyl)-phenyl]propionamide A solution of 2.76 gm (13 mmole) of 4-carbomethoxy-2-methoxybenzylmercaptan in 70 ml of THF at o, was treated with 520mg (13 mmole) 60% NaH. A solution of 3.51 gm (10 mmole) of the compound of Example 19(d) in 100 ml of $CH_2Cl_2$ at 0° was treated with 7.43 ml (25 mmole) of titanium isopropoxide. The two solutions were combined and stirred at 0° for 2 hours, at 20° for 16 hours, and quenched with 100 ml of 10% $H_2SO_4$. The mixture was extracted with $CH_2Cl_2$. The extracts were washed with $H_2O$, dried, and the solvent evaporated. The residue was chromatographed over a silica column, and 3.4 gm of product was eluted with a mixture of 5% MeoH and 95% EtOAc.

(b) Methyl[R-(R*,S*)]-3-[(4-carbomethoxy-2-methoxy phenylmethyl)thiol-2-hydroxy-3[2-(8-phenyloctyl) phenyl]propionate This compound is prepared from the compound of Example 22(a) in a manner exactly analagous to the preparation of the compound of Example 19(f). nmr($CDCl_3$):6.92–7.78(m,12H), 4.70(t,1H), 4.50(d,1H), 3.60–3.93(d of d, 2H), 3.90(s,3H), 3.87(s,3H), 3.60(s,3H), 3.30(d,1H), 2.58(t,2H), 2.20–2.46(m,2H), .98–1.72(m,12H).

(c) [R-(R*,S*)]-3-[(4-carboxy-2-methoxyphenylmethyl)thiol-2-hydroxy-3-[2-(8-phenyloctyl) phenyl]propionic acid This compound was prepared from the compound of Example 22(b) in a manner exactly analagous to the preparation of the compound of Example 20.

nmr($CDCl_3/Me_2Co$): 6.93–7.78(m,12H), 4.76(d,1H), 4.53(d,1H), 3.92(d,1H), 3.82(s,3H), 3.68(d,1H), 2.24–2.69(m,4H), 1.03–1.80(m,12H).

EXAMPLE 23

Preparation of [R-(R*,S*)]-3-[(4-carboxy-2-fluorophenylmethyl)thio]-thio]-2-hydroxy-3-[2-(8-phenyloctyl)phenyl]-propionic acid (a) [R-(R*,S*)]-3-[(4-carbomethoxy-2-fluorophenylmethyl)thio]-2-hydroxy-3-[2-(8-phenyloctyl)phenyl]-propionamide This compound was prepared from the compound of Example 19(c) in a manner exactly analagous to that of Example 22.

(b) Methyl [R-(R*,S*)]-3-1(4-carbomethoxy-fluorophenylmethyl)thio]-2-hydroxy-3-[2-(8-phenyloctyl)-phenyl]propionate This compound was prepared from the compound of Example 23(a) in a manner exactly analagous to the preparation of Example 19(f).

nmr($CDCl_3$): 6.97–7.90(m,12H), 4.42–4.72(m,2H), 3.48–3.98(m,8H), 3.06(d,1H), 2.28–2.72(m,4H), 1.00–1.749m,12H).

(c) [R-(R*,S*)]-3-[(4-carboxy-2-fluorophenylmethyl)-thio]-2-hydroxy-3-[2-(8-phenyloctyl)phenyl]propionic acid This compound was prepared from the compound of Example 23(b) in a manner exactly analagous to the preparation of the compound of Example 20.

nmr($CDCl_3$): 6.98–7.90(m,12H), 4.68(d,1H), 4.55(d,1H), 3.60–3.92(m,2H), 2.20–2.70(m,4H), 1.02–1.76 (m,12H).

EXAMPLE 24

Preparation of [R-(R*,S*)]-3-[(3-carboxymethylphenyl)thio]-2-hydroxy-3-[2-(8-phenyloctyl)phenyl]propionic acid (a) [R-(R*,S*)]-3-[(3-carbomethoxymethylphenyl)-thio]-2-hydroxy-3-12-(8-phenyloctyl)phenyl]propionamide This compound was prepared from the compound of Example 19(d) and methyl-m-mercaptophenylacetate in a manner exactly analagous to the preparation of the compound of Example 22(a).

nmr($CDCl_3$): 7.58–7.82(m,1H), 6.96–7.52(m,12H), 6.39(broad d, 1H), 5.62(broad d,1H), 5.05(d,1H), 4.37(t,1H), 4.08(d,1H), 3.70(s,3H), 3.58(s,2H), 2.50–3.02(m,4H), 1.18–1.82(m,12H).

(b) Methyl [R-(R*,S*)]-3-1(3-carbomethoxymethyl phenyl)thio]-2-hydroxy-3-[2-(8-phenyloctyl) phenyl]-propionate This compound was prepared from the compound of Example 24(a) in a manner exactly analagous to the preparation of the compound of Example 19(f).

(c) [R-(R*,S*)]-3-[(3-carboxymethylphenyl)thio]-2-hydroxy-3-[2-(8-phenyloctyl)phenyl]propionic acid This compound was prepared from the compound of Example 24(b) in a manner exactly analagous to the preparation of the compound of Example 20.

nmr($CDCl_3$): 7.50–7.78(m,1H), 6.72–7.48(m,12H), 4.90(d,1H), 4.50(d,1H), 3.52(s,2H), 2.32–2.86(m,4H), 0.94–1.72(m,12H).

EXAMPLE 25

As a specific embodiment of a composition of this invention, 1 to 10 mg/ml of an active ingredient, such as the compound of Example 1 is dissolved in isotonic saline solution and aerosolized from a nebulizer operating at an air flow adjusted to deliver the desired aerosolized weight of drug.

EXAMPLE 26

As an additional embodiment of a composition of this invention 100 mg of an active ingredient, such as the compound of Example 4, 13, or 14 is combined with 4 mg of chlorpheniramine maleate with a suitable carrier or excipient.

What is claimed is:

1. A compound represented by the following structural formula (I):

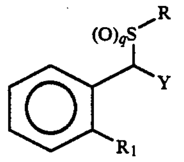

(I)

wherein q is 0, 1 or 2;

$R_1$ is $(L)_a$—$CH_2)_b$—$(T)_c$—M a is 0 or 1;

b is 3 to 14;

c is 0 or 1;

L and T are independently sulfur, oxygen, or $CH_2$ with the proviso that L and T are not sulfur when q is 1 or 2; and M is $C_{10}$4alkyl, ethynyl, trifluoromethyl, isopropenyl, thienyl, cyclohexyl or phenyl unsubstituted or monosubstituted with Br, Cl, $CF_3$, $C_{1-4}$alkoxy, $C_{1-4}$alkyl, methylthio, or trifluoromethylthio;

Y is $(CHX)_n(CH_2)_p$—Z wherein $R_3$ is OH, $NH_2$, aryloxy, or $C_{1-6}$alkoxy;

n is 0 or 1;

p is 0 or 1;

X is H, OH, $C_{1-4}$alkyl, $C_{1-4}$alkoxy, or F; and

Z is $COR_3$, or tetrazolyl;

R is

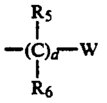

$R_5$ and $R_6$ are independently hydrogen or $C_{1-4}$alkyl at any point when d is not O;

d is 0 to 6;

W is phenyl, unsubstituted or substituted with B, C, or D; or W is

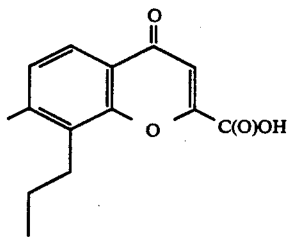

B is

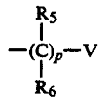

wherein $R_5$ and $R_6$ are independently hydrogen or $C_{1-4}$alkyl;

p is 0 to 6;

V is H, C1-4alkyl, $COR_3$, $SO_3H$, $SO_2H$, $SO_2NH_2HN_2$, $COCH_2OH$, $CHOHCH_2OH$, or tetrazolyl, with $R_3$ as defined above;

C and D are independently selected from H, OH, F, Cl, Br, $CF_3$, $C_{1-4}$alkyl, $C_{1-4}$ alkoxy, methylthio, trifluoromethylthio, $NO_2$, $NH_2$, $NHC_{1-4}$alkyl, or $C_{1-4}$alkylCO-; or a pharmaceutically acceptable salt thereof.

2. A compound of claim 1 represented by the following structural formula:

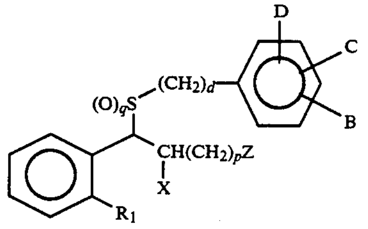

wherein $R_1$, B, C, D, X, Z, p, q, and d are as defined in claim 1, or a pharmaceutically acceptable salt thereof.

3. A compound of claim 1 which is 2-hydroxy-3-(4-carboxyphenylthio)-3-[2-(8-phenyloctyl)phenyl]propionic acid.

4. A compound of claim 1 represented by the following structural formula:

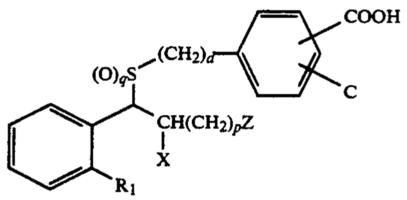

wherein $R_1$, B, C, D, X, Z, p, q, and d are as defined in claim 1, or a pharmaceutically acceptable salt thereof.

5. A compound of claim 4 which is:

2-hydroxy-3-(2-carboxyphenylthio)-3-[2-(8-phenyloctyl)phenyl]propionic acid;

2(S)-hydroxy-3(R) (2-carboxyphenylmethylthio)-3-[2-(8-phenyloctyl)phenyl]propionic acid;

2(S)-hydroxy-3(R)-(3-carboxyphenylmethylthio)-3-[2-(8-phenyloctyl)phenyl]propionic acid;

2-hydroxy-3-(3-carboxyphenylthio)-3-[2-(8-phenyloctyl)phenyl]propionic acid;

2-hydroxy-3-(4-carboxyphenylthio)-3-[2-(8-phenyloctyl)phenyl]propionic acid;

2-hydroxy-3-(4-carboxy-2-methoxyphenylmethylthio)-3-[2-(8-phenyloctyl)phenyl]propionic acid;

2-hydroxy-3-(4-carboxyphenylmethylthio)-3-[2-(8-phenyloctyl)phenyl]propionic acid;

2-hydroxy-3-(2-fluoro-4-carboxyphenylmethylthio)-3-[2-(8-phenyloctyl)phenyl]propionic acid;

2-methoxy-3-(4-carboxyphenylthio)-3-[2-(8-phenyloctyl)phenyl]propionic acid;

2-methoxy-3-[4-carboxy-2-methoxyphenylmethylthio)-3-[2-(8-phenyloctyl)-phenyl]propionic acid;

2-hydroxy-3-(5-carboxy-2-methoxy-phenylmethylthio)-3-[2-(8-phenyloctyl)phenyl]propionic acid;

[R-(R*,S*)]-3-[4-carboxyphenyl)thio]-2-methoxy-3-[2-(8-phenyloctyl)phenyl]propionic acid;

[R-(R*,S*)]-3-[(4-carboxyphenyl)thio]-2-hydroxy-3-[2-(8-phenyloctyl)phenyl]propionic acid;

[R-(R*,S*)]-3-[(4-carboxy-2-methoxyphenylmethyl)thio]-2-hydroxy-3-[2-(8-phenyloctyl)phenyl]propionic acid;

[R-(R*,S*)]-3-[(4-carboxy-2-fluorophenylmethyl)thio]-2-hydroxy-3-[2-(8-phenyloctyl)phenyl]propionic acid;

[R-(R*,S*)]-3-[3-carboxymethylphenyl)thio]-2-hydroxy-3-[2-(8-phenyloctyl)phenyl]propionic acid.

6. A compound of claim 1 which is [R-(R*,S*)]-3-[(4-carboxyphenyl)sulfonyl]-2-methoxy-3-[2-(8-phenyloctyl)phenyl]propionic acid or a pharmaceutically acceptable salt thereof.

7. A compound of claim 1 represented by the following structural formula:

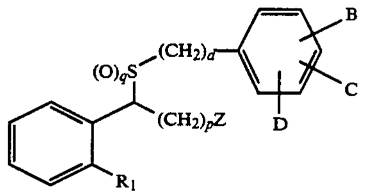

wherein $R_1$, B, C, D, X, Z, p, q, and d are as defined in claim 1, or a pharmaceutically acceptable salt thereof.

8. A compound of claim 7 which is 3-(4-carboxy-2-methoxyphenylmethylthio)-3-[2-(8-phenyloctyl)-phenyl]propionic acid.

9. A compound of claim 1 represented by the following structural formula:

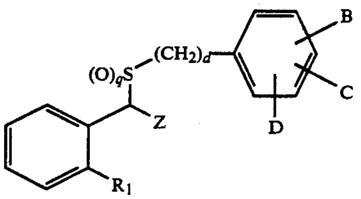

wherein $R_1$, B, C, D, X, Z, p, q, and d are as defined in claim 1, or a pharmaceutically acceptable salt thereof.

10. A pharmaceutical composition comprising a pharmaceutical carrier or diluent and an effective amount of a compound of claim 1.

11. The composition of claim 10 wherein the compound if 3-[(4-carboxyphenyl)sulfonyl]-2-methoxy-3-[2-(8-phenyloctyl)-phenyl]propionic acid or a pharmaceutically acceptable salt thereof.

12. The composition of claim 10 in a form suitable for administering orally, parenterally, topically, or by inhalation.

13. The composition of claim 12 in which the active ingredient is 2-hydroxy-3-[(2-methoxy-4-carboxyphenylmethylthio(]-3-[2-(8-phenyloctyl)phenyl]propionic acid or a pharmaceutically acceptable salt.

14. The composition of claim 12 in which the active ingredient is [R-(R*,S*)]3-[(4-carboxyphenyl)sulfonyl]-2-methoxy-3-[2-(8-phenyloctyl)phenyl]propionic acid or a pharmaceutically acceptable salt.

15. A method of treating diseases in which leukotrienes are a factor in a subject in need thereof comprising administering to such subject an effective non-toxic amount of the pharmaceutical composition of claim 10.

* * * * *